US008535718B2

(12) United States Patent
Dansereau et al.

(10) Patent No.: US 8,535,718 B2
(45) Date of Patent: *Sep. 17, 2013

(54) DOSAGE FORMS OF BISPHOSPHONATES

(75) Inventors: Richard John Dansereau, Cincinnati, OH (US); David Ernest Burgio, Jr., Liberty Township, OH (US)

(73) Assignee: Warner Chilcott Company, LLC., Fajardo, PR (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/544,377

(22) Filed: Jul. 9, 2012

(65) Prior Publication Data

US 2013/0012478 A1 Jan. 10, 2013

Related U.S. Application Data

(63) Continuation of application No. 12/637,100, filed on Dec. 14, 2009, now Pat. No. 8,246,989, which is a continuation of application No. 11/106,816, filed on Apr. 15, 2005, now Pat. No. 7,645,459.

(60) Provisional application No. 60/573,881, filed on May 24, 2004.

(51) Int. Cl.
*A61K 9/28* (2006.01)

(52) U.S. Cl.
USPC .............. 424/474; 424/465; 424/468; 514/89

(58) Field of Classification Search
None
See application file for complete search history.

(56) References Cited

U.S. PATENT DOCUMENTS

| | | |
|---|---|---|
| 5,167,947 A | 12/1992 | Geary |
| 5,296,475 A | 3/1994 | Flesch et al. ............... 514/108 |
| 5,304,377 A | 4/1994 | Yamada et al. ............. 424/426 |
| 5,356,887 A | 10/1994 | Brenner et al. |
| 5,431,920 A | 7/1995 | Bechard ...................... 424/480 |
| 5,438,048 A | 8/1995 | Nikander et al. |
| 5,462,932 A | 10/1995 | Brenner et al. ............. 514/108 |
| 5,622,721 A | 4/1997 | Dansereau et al. .......... 424/490 |
| 5,686,106 A | 11/1997 | Kelm et al. ................. 424/463 |
| 5,735,810 A | 4/1998 | Sage, Jr. et al. |
| 5,853,759 A | 12/1998 | Katdare et al. ............. 424/466 |
| 5,935,602 A | 8/1999 | Dansereau et al. |
| 6,143,326 A | 11/2000 | Mockel et al. .............. 424/482 |
| 6,200,602 B1 | 3/2001 | Watts et al. ................. 424/463 |
| 6,248,363 B1 | 6/2001 | Patel et al. .................. 424/497 |
| 6,309,663 B1 | 10/2001 | Patel et al. .................. 424/450 |
| 6,333,316 B1 | 12/2001 | Daifotis et al. ............. 514/108 |
| 6,368,629 B1 | 4/2002 | Watanabe et al. ........... 424/482 |
| 6,416,737 B1 | 7/2002 | Manolagas et al. .......... 424/9.2 |
| 6,432,932 B1 | 8/2002 | Daifotis et al. ............. 514/108 |
| 6,468,559 B1 | 10/2002 | Chen et al. ................. 424/451 |
| 6,506,407 B2 | 1/2003 | Watanabe et al. .......... 424/463 |
| 6,623,755 B2 | 9/2003 | Chen et al. ................. 424/464 |
| 6,676,965 B1 | 1/2004 | Lulla et al. ................. 424/458 |
| 6,677,320 B2 | 1/2004 | Diederich et al. .......... 514/102 |
| 7,309,698 B2 | 12/2007 | Boyd et al. ................. 514/102 |
| 7,645,459 B2 | 1/2010 | Dansereau et al. .......... 424/474 |
| 7,645,460 B2 | 1/2010 | Dansereau et al. .......... 424/474 |
| 8,409,614 B2 | 4/2013 | Dansereau et al. |
| 8,409,615 B2 | 4/2013 | Dansereau et al. |
| 2001/0036475 A1 | 11/2001 | Chen et al. ................. 424/465 |
| 2003/0158154 A1 | 8/2003 | Fleshner-Barak ............. 514/89 |
| 2003/0203878 A1 | 10/2003 | Flashner-Barak et al. ...... 514/89 |
| 2005/0070504 A1 | 3/2005 | Burgio et al. |
| 2005/0089573 A1 | 4/2005 | Moeckel et al. ............. 424/471 |
| 2005/0182028 A1 | 8/2005 | Chen .............................. 514/89 |
| 2005/0226907 A1 | 10/2005 | Moneymaker et al. ....... 424/439 |
| 2005/0260262 A1 | 11/2005 | Dansereau et al. .......... 424/464 |
| 2006/0069069 A1 | 3/2006 | Kajander et al. .............. 514/89 |
| 2006/0110452 A1 | 5/2006 | Dansereau et al. .......... 424/464 |
| 2006/0134190 A1 | 6/2006 | Kim et al. ................... 424/451 |
| 2006/0210639 A1 | 9/2006 | Liversidge et al. .......... 424/489 |
| 2006/0263355 A1 | 11/2006 | Quan et al. ................ 424/141.1 |
| 2007/0003512 A1 | 1/2007 | Stockel et al. .............. 424/76.1 |
| 2007/0238707 A1 | 10/2007 | Leonard ........................ 514/89 |
| 2008/0286359 A1 | 11/2008 | Dansereau et al. .......... 424/474 |
| 2008/0287400 A1 | 11/2008 | Dansereau et al. ............ 514/87 |

(Continued)

FOREIGN PATENT DOCUMENTS

| | | |
|---|---|---|
| BR | 106601-3 | 9/2003 |
| EP | 0449405 A2 | 10/1991 |

(Continued)

OTHER PUBLICATIONS

Decision revoking the European Patent issued in the Opposition of European Patent No. 1753395, dated Nov. 19, 2012.
Boulenc, X. et al., "Importance of the paracellular pathway for the transport of a new bisphosphonate using the human CACO-2 monolayers model," Biochemical Pharmacology, vol. 46, No. 9, pp. 1591-1600 (1993).
Boulenc, X. et al., "Bisphosphonates increase tight junction permeability in the human intestinal epithelial (Caco-2) model", International J. of Pharmaceutics, vol. 123, pp. 13-24 (1995).

(Continued)

*Primary Examiner* — Jake Vu
(74) *Attorney, Agent, or Firm* — Fitzpatrick, Cella, Harper & Scinto

(57) ABSTRACT

Provided is an oral dosage form comprising a bisphosphonate selected from the group consisting of a risedronate and salts thereof; an ethylenediaminetetraacetic acid (EDTA) or a pharmaceutically acceptable salt thereof; and a delayed release mechanism to deliver the risedronate and the EDTA in the lower gastrointestinal tract, wherein the oral dosage form is administered according to a scheduled dosing interval. The present invention substantially alleviates the interaction between bisphosphonates and food or beverages, which interaction results in the bisphosphonate active ingredient not being available for absorption. The resulting oral dosage form may thus be taken with or without food. Further, the present invention effects delivery of the bisphosphonate and the chelating agent to the lower GI tract, substantially alleviating the upper GI irritation associated with bisphosphonate therapies. These benefits simplify previously complex treatment regimens and can lead to increased patient compliance with bisphosphonate therapies.

12 Claims, No Drawings

(56) References Cited

U.S. PATENT DOCUMENTS

| | | | |
|---|---|---|---|
| 2010/0086593 A1 | 4/2010 | Dansereau et al. | ........... 424/474 |
| 2010/0119559 A1 | 5/2010 | Dansereau et al. | |
| 2012/0094960 A1 | 4/2012 | Dansereau et al. | |
| 2013/0012478 A1 | 1/2013 | Dansereau et al. | |

FOREIGN PATENT DOCUMENTS

| | | |
|---|---|---|
| EP | WO 93/09785 | 5/1993 |
| EP | WO 97/44017 | 11/1997 |
| EP | WO 01/32185 A1 | 5/2001 |
| IN | 2004MU01360 A | 7/2006 |
| JP | 7-501073 | 2/1995 |
| JP | 8092102 | 4/1996 |
| JP | 9-504276 | 4/1997 |
| WO | WO 93/09785 | 5/1993 |
| WO | WO 93/21907 | 11/1993 |
| WO | WO 97/44017 | 11/1997 |
| WO | WO 98/14196 A1 | 4/1998 |
| WO | WO 99/02539 A1 | 1/1999 |
| WO | WO 00/61111 | 10/2000 |
| WO | WO 01/02155 A1 | 2/2001 |
| WO | WO 01/32185 | 5/2001 |
| WO | WO 01/52859 | 7/2001 |
| WO | WO 01/76577 | 10/2001 |
| WO | WO 01/82903 | 11/2001 |
| WO | WO 03/002151 | 1/2003 |
| WO | WO 03/007916 | 1/2003 |
| WO | WO 03/051373 A1 | 6/2003 |
| WO | WO 2004/065397 | 8/2004 |
| WO | WO 2005/016872 | 5/2005 |
| WO | WO 2006/019843 | 2/2006 |
| WO | WO 2006/020009 | 2/2006 |

OTHER PUBLICATIONS

Bronner, F. et al., "Nutritional Aspects of Calcium Absorption", J. Nutr., vol. 129, pp. 9-12 (1999).
Dowty, M. et al., APPS Annual Meeting, San Francisco, Nov. 19, 1998.
Ezra, A. et al., "Administration routes and delivery systems of bisphosphonates for the treatment of bone resorption", Drug Delivery Review, vol. 42, pp. 175-195 (2000).
Gertz, B.J. et al., "Studies of the oral bioavailability of alendronate", Clinical Pharmacology & Therapeutics, vol. 58, No. 3, pp. 288-298 (1995).
Green, J.R. et al., "The effect of zoledronate and pamidronate on the intestinal permeability barrier in vitro and in vivo", International J. of Pharmaceutics, vol. 153, pp. 59-66 (1997).
Janner, M. et al., "Sodium EDTA Enhances Intestinal Absorption of Two Bisphosphonates", Calcified Tissue International, vol. 49, pp. 280-283 (1991).
Kinget, R. et al., "Colonic drug targeting", J. of Drug Targeting, 1998, vol. 6, No. 2, pp. 129-149 (1998).
Lin, J.H. et al., "On the Absorption of Alendronate in Rats", J. of Pharmaceutical Sciences, vol. 83, No. 12, pp. 1741-1746 (1994).
Mahe, S. et al., "Gastroileal nitrogen and electrolyte movements after bovine milk ingestion in humans", Am. J. Clin. Nutr., vol. 56, pp. 410-416 (1992).
Mitchell, D. et al., "The effect of dosing regimen on the pharmacokinetics of risedronate", Br. J. Clin. Pharmacol., vol. 48, pp. 536-542 (1998).
Mitchell, D. et al., "Risedronate Gastrointestinal Absorption is Independent of Site and Rate of Administration", Pharm. Res., vol. 15, No. 2, pp. 228-232 (1998).
Muranishi, S., "Absorption Enhancers", Critical Reviews in Therapeutic Drug Carrier Systems, vol. 7, No. 1, pp. 1-33 (1990).
Nykanen, P. et al., "Citric acid as excipient in multiple-unit enteric-coated tablets for targeting drugs on the colon", International J. of Pharmaceutics, vol. 229, No. 1-2, pp. 155-162 (2001).
Perez-Millan, "Subserosal Eosinophilic Gastroenteritis Treated Efficaciously with Sodium Cromoglycate," Digestive Diseases and Sciences, vol. 42, No. 2, (1997).
Poiger, H. et al., "Compensation of dietary induced reduction of teracycline absorption by simultaneous administration of EDTA", Europ. J. Clin. Pharmacol, vol. 14, pp. 129-131 (1978).
Raiman, J. et al., "Effects of various absorption enhancers on transport of clodronate through caco-2 cells," International Journal of Pharmaceutics, vol. 261, pp. 129-136 (2003).
Rowe, R.C. (Ed.), "Edetic Acid", Handbook of Pharmaceutical Excipients, pp. 225-228 (2002).
Simon, et al., "The effect of clodronate on the integrity and viability of rat small intestine in vitro—a comparison with EDTA," Biological Pharmaceutical Bulletin, vol. 28, No. 7, pp. 1249-1253. Journal code: 9311984. ISSN:0918-6158 (2005).
Swenson, E.S. et al., "(C) Means to enhance penetration (2) Intestinal permeability enhancement for proteins, peptides and other polar drugs: mechanisms and potential toxicity", Advanced Drug Deliver Reviews, vol. 8, pp. 39-92 (1992).
Tomita, M. et al., "Absorption-enhancing mechanism of EDTA, Caprate, and Decanoylcarnitine in Caco-2 cells", J. of pharmaceutical Sciences, vol. 85, No. 6, pp. 608-611 (1996).
Watts, P.J. et al., "Colonic drug delivery", Drug Development and Industrial Pharmacy, 1997, vol. 23, No. 9, pp. 893-913 (1997).
Whittaker, P. et al., "Toxicological profile, current use, and regulatory issues on EDTA compounds for assessing use of sodium iron EDTA for food fortification", Regulatory Toxicology and Pharmacology, vol. 18, pp. 419-427 (1993).
PCT International Search Report dated Dec. 7, 2005.
Notice of Opposition filed by Apotex Inc. on Apr. 26, 2011 against European Patent No. 1753395 (22 pages).
Response to Opposition of European Patent No. 1753395, filed by Warner Chilcott Company, LLC on Dec. 1, 2011 (5 pages).
Cassidy, M.M. et al., "Cellular Mechanism of Intestinal Permeability Alterations Produced by Chelation Depletion," J. Cell Bio., 32:685-98 (1967).
Chung, R.S.K., et al., "Effects of Chelation of Calcium on the Gastric Mucosal Barrier," Gastroenterology; 59(2):200-07 (1970).
Rosenblatt, D.E., et al., "Calcium Ethylenediaminetetraacetate (CaEDTA) Toxicity: Time- and Dose-Response Studies on Intestinal Morphology in the Rat," Experimental and Molecular Pathology, 28(2):215-26 (1978).
"Edetic Acid," Kibbe, A.H., Ed., Handbook of Pharmaceutical Excipients, Third Edition, Pharmaceutical Press and American Pharmaceutical Association, London, GB and Washington, DC, 191-4 (2000).
Complaint for Patent Infringement by Warner Chilcott Company, LLC and Warner Chilcott (US), LLC against Teva Pharmaceuticals USA, Inc. and Teva Pharmaceuticals Industries Ltd. filed Nov. 22, 2011 (10 pages).
Complaint for Patent Infringement by Warner Chilcott Company, LLC and Waner Chilcott (US), LLC against Watson Pharmaceuticals, Inc., Watson Laboratories, Inc.—Florida, and Watson Pharma, Inc. filed Oct. 12, 2011 (12 pages).
Watson Laboratories, Inc.—Florida's Answer, Separate Defenses, and Amended Counterclaims to Plaintiffs' Complaint filed Jan. 4, 2012 (13 pages).
Russell, R.G., et al., "Bisphosphonates an Update on Mechanisms of Action and How These Relate to Clinical Efficacy," Ann. N.Y. Acad. Sci., 1117:209-257 (2007).
Nancollas, G.H., et al., "Novel Insights into Action of Bisphosphonates on Bone: Differences in Interactions with Hydroxyapatite," Bone, 38: 617-627 (2005).
Dunford, J.E., et al., "Structure-Activity Relationships for Inhibition of Farnesyl Diphosphate Synthase in Vitro and Inhibition of Bone Resorption in Vivo by Nitrogen-Containing Bisphosphonates," The Journal of Pharmacology and Experimental Therapeutics, 296(2): 235-242 (2001).
Fleisch, H., "Chemistry and Mechanisms of Action of Bisphosphonates," Bone Resorption, Metastasis, and Diphosphonates, Silvio Garattini, ed., Raven Press, New York, pp. 33-40 (1985).
Teva Pharmaceutical's Notice of Paragraph IV Certification concerning Risedronate-Sodium Delayed-Release Tablets, Oct. 13, 2011.

Watson Laboratories, Inc.—Florida's Notification of Certification of Invalidity and/or Non-infringement of U.S. Patent Nos. 7,645,459 and 7,645,460, Aug. 29, 2011.
PDR (Physicians' Desk Reference: 55th edition (2001), p. 331).
Office Action issued in Japanese Application No. 2008-506437 (Mar. 29, 2011) (2 pages).
"Actonel (risedronate sodium tablets),"label (May 2002).
Katsuma et al., "Scintigraphic Evaluation of a Novel Colon-Targeted Delivery System (CODES-TM) in Healthy Volunteers," J. Pharm. Sci. 93(5) 1287-99 (2004).
Lin et al., "Factors Affecting Oral Absorption of Alendronate, a Potent Antiosteolytic Bisphosphonate in Rats," Pharm. Research, 8:S273 (1991).
Atelvia (risedronate sodium delayed-release tablets) Highlights of Prescribing Information, 25 pages, revised Oct. 2010.
Vasikaran, "Bisphosphonates: an overview with special reference to alendronate," Ann. Clin. Biochem. 38:608-23 (2001).
Wasserman, "Vitamin D and the Dual Processes of Intestinal Calcium Absorption," J. Nutr., 134:3137-39 (2004).
Beme et al., Chapter 31: Gastrointestinal Regulation and Motility, pp. 539-565, Physiology, Mosby Publishing (5th Ed., 2004).
Fordtran et al., "Ionic Constituents and Osmolality of Gastric Emptying and Small-Intestinal Fluids after Eating," Am. J. Dig. Dis., 11:503-21 (1966).
Lindahl et al., "Characterization of Fluids from the Stomach and Proximal Jejunum in Men and Women," Pharm. Res., 14:497-502 (1997).
Phillips et al., "The Contribution of the Colon to Electrolyte and Water Conservation in Man," J. Lab. Clin. Med., 81:733-46 (1973).
Lenter, Gergy Scientific Tables, vol. 1: Units of Measurement, Body Fluids, Composition of the Body, Nutrition, pp. 123-58 (1981).
Fransson et al., "Distribution of Trace Elements and Minerals in Human and Cow's Milk," Ped. Res., 17:912-15 (1983).
Wilding et al., "The Role of Gamma Scintigraphy in Oral Drug Delivery," Adv. Drug. Delivery Rev., 7:87-117 (1991).
Rao et al., Chapter 25: The Stomach, Pylorus and Duodenum, pp. 373-392, An Illustrated Guide to Gastrointestinal Motility, Kumar and Wingate eds., Churchill Livingstone (2nd Ed., 1993).
Bueno et al., Chapter 10: Food and Gastrointestinal Motility, pp. 130-143, An Illustrated Guide to Gastrointestinal Motility, Kumar and Wingate eds., Churchill Livingstone (2nd Ed., 1993).
Lee et al. "MR Imaging of the Small Bowel Using the HASTE sequence," Am. J. Roentgenol., 170(6):1457-63 (1998).
Lachman, "Antioxidants and Chelating Agents as Stabilizers in Liquid Dosage Forms, " The Indian Journal of Pharmacy, 30:109-119 (1968).
Skoog et al., The Fundamentals of Analytical Chemistry, pp. 281-283, Saunders College Publishing, (7th ed., 1996).
Lin, "Bisphosphonates: A Review of Their Pharmacokinetic Properties", Bone, 18:75-85 (1996).
Fleisch "Bisphosphonates in Bone Disease," Stampli & Co., Bern, p. 50 (1993).
Sakuma, "Effect of Administration Site in the Gastrointestinal Tract on Bioavailability of Poorly Absorbed Drugs Taken After Meal," J. Controlled Release, 118:59-64 (2007).
Lenter, Gergy Scientific Tables, vol. 1: Units of Measurement, Body Fluids, Composition of the Body, Nutrition, pp. 241-266 (1981).
World Health Organization Technical Report Series No. 539, Toxicological Evaluation of Certain Food Additives with a Review of General Principles and of Specifications, Seventeenth Report of the Joint FAO/WHO Expert Committee on Food Additives, pp. 1-40 (1974).
Guidance for Industry and Reviewers. Estimating the Safe Starting Dose in Clinical Trials for Therapeutics in Adult Healthy Volunteers, Draft Guidance, pp. 1-26 (Dec. 2002).
Guidance for Industry. Estimating the Maximum Safe Starting Dose in Initial Clinical Trials for Therapeutics in Adult Healthy Volunteers, pp. 1-27 (Jul. 2005).
FDA, Approved Drug Products with Therapeutic Equivalence Evaluations, 23rd Edition (2003), 5 pages.
Summons to Attend Oral Proceedings pursuant to Rule 115(1) EPC in the Opposition against a related European Patent No. 1753395, issued on Mar. 23, 2012 (8 pages).
Decision revoking the European Patent issued in Opposition of European Patent No. 1753395, dated Nov. 19, 2012.
Provision of the minutes from the oral proceeding in the Opposition of European Patent No. 1753395, dated Nov. 19, 2012.
Grounds of Appeal and accompanying Appeal Brief submitted in Appeal T0177/13-3.3.07 against revocation of European Patent No. 1753395, dated Mar. 28, 2013.
Contreras, R.G., et al, "Calcium and Tight Junctions," Chapter 10, Tight Junctions, Marcelino Cereijido, ed., CRC Press, pp. 139-149 (1992).
Wilding, I., "The Oral Magic Bullet: Remote Controlled Micro-Electronic Capsules for Delivering Drug at the Right Place at the Right Time," Pharmaceutical Profiles, Power Point presentation (Dec. 2004).
Wilding, I., "The Enterion Capsule: A Novel Technology for Understanding the Biopharmaceutical Complexity of New Molecular Entities (NMEs)," Drug Development & Delivery, vol. 1, No. 1 (2001).
Declaration of Hans Junginger, Ph.D., dated Mar. 25, 2013.
Declaration of David E. Burgio, Ph.D., dated Mar. 20, 2013.
Mitchell, D.Y. et al., "Bioavailability of Immediate-Release and Delayed-Release Risedronate Formulations Upon Oral Administration to Healthy Male Subjects in Fasted and Fed State," Pharmaceutical Reasearch, vol. 13, No. 9, Abstract PPDM 8263, p. S-458 (1996).
U.S. Appl. No. 13/778,989, filed Feb. 27, 2013.
U.S. Appl. No. 13/782,495, filed Mar. 1, 2013.

DOSAGE FORMS OF BISPHOSPHONATES

CROSS REFERENCE TO RELATED APPLICATIONS

This application is a continuation of application Ser. No. 12/637,100, filed Dec. 14, 2009, which is a continuation of application Ser. No. 11/106,816, filed Apr. 15, 2005, now U.S. Pat. No. 7,645,459, which claims priority under Title 35, United States Code 119(e) from Provisional Application Ser. No. 60/573,881, May 24, 2004 and incorporates by reference the entire disclosure of each of the mentioned prior applications.

FIELD OF THE INVENTION

The present invention relates to oral dosage forms of a bisphosphonate comprised of a safe and effective amount of a pharmaceutical composition comprising a bisphosphonate, a chelating agent for enabling administration of the bisphosphonate active ingredient with food or beverages, means for effecting delayed release of the bisphosphonate and the chelating agent in the lower gastrointestinal tract, and one or more pharmaceutically-acceptable excipients. The oral dosage forms of the invention provide delivery of the pharmaceutical composition to the lower gastrointestinal tract of the mammal subject and provide pharmaceutically effective absorption of the bisphosphonate when administered with or without food or beverages. The present invention further relates to a method of treating or preventing diseases characterized by abnormal calcium and phosphate metabolism comprising administering to a human or other mammal in need thereof the oral dosage form described herein.

BACKGROUND OF THE INVENTION

Bisphosphonates were first developed to complex calcium in hard water to improve detergent performance. Bisphosphonates have since been found to be useful in the treatment and prevention of diseases or conditions characterized by abnormal calcium and phosphate metabolism. Such conditions may be divided into two broad categories:

1. Conditions which are characterized by anomalous mobilization of calcium and phosphate leading to general or specific bone loss or excessively high calcium and phosphate levels in the fluids of the body. Such conditions are sometimes referred to herein as pathological hard tissue demineralization.

2. Conditions which cause or result from deposition of calcium and phosphate anomalously in the body. These conditions are sometimes referred to herein as pathological calcifications.

The first category includes osteoporosis, a condition in which bone hard tissue is lost disproportionately to the development of new hard tissue. Essential quantities of cancellous bone are lost, and marrow and bone spaces become larger, resulting in reduced cancellous bone strength. Bone also becomes less dense and fragile. Osteoporosis can be sub-classified as senile, drug induced (e.g., adrenocorticoid, as can occur in steroid therapy), disease induced (e.g., arthritic and tumor), etc., however the manifestations are similar. Another condition in the first category is Paget's disease (osteitis deformans). In this disease, dissolution of normal bone occurs, which is then haphazardly replaced by soft, poorly mineralized tissue such that the bone becomes deformed from pressures of weight bearing, particularly in the tibia and femur. Hyperparathyroidism, hypercalcemia of malignancy, and osteolytic bone metastasis are conditions also included in the first category.

The second category, involving conditions manifested by anomalous calcium and phosphate deposition, includes myositis ossificans progressiva, calcinosis universalis, and such afflictions as arthritis, neuritis, bursitis, tendonitis, and other inflammatory conditions which predispose involved tissue to deposition of calcium phosphates.

Bisphosphonates tend to inhibit the resorption of bone tissue, which is beneficial to patients suffering from excessive bone loss. However, many of the early bisphosphonates, such as ethane-1,1-diphosphonic acid (EHDP), propane-3-amino-1-hydroxy-1,1-diphosphonic acid (APD), and dichloromethane diphosphonic acid (Cl$_2$MDP), have the propensity of inhibiting bone mineralization when administered at high dosage levels. Although more biologically potent bisphosphonates exist, which can be administered at lower dosage levels (such as 1-hydroxy-2-(3-pyridinyl)-ethylidene-1,1-bisphosphonic acid (risedronate), alendronate, ibandronate, and zoledronate), oral administration of bisphosphonates sometimes results in patient complaints shortly after dosing. These complaints are usually characterized by the patients as heartburn, esophageal burning, pain and/or difficulty upon swallowing, and/or pain existing behind and/or mid-sternum. It is hypothesized that this irritation results from the bisphosphonate tablet adhering to epithelial and mucosal tissues, resulting in the topical irritation thereof. In order to avoid potential upper gastrointestinal irritation, patients taking bisphosphonates are instructed to take their medication with a full glass of water, and to remain upright for at least thirty minutes after taking an oral dose of a bisphosphonate.

It is known that oral doses of bisphosphonates are poorly absorbed (less than 1% of the oral dose) in the gastrointestinal (GI) tract. See Ezra et al., Adv. Drug Del. Rev. 42: 175-95 (2000). Several approaches have been suggested for increasing absorption of oral bisphosphonates throughout the GI tract. These approaches include modifying the permeability properties of the intestinal mucosa (e.g., through the use of absorption enhancers), or altering the physical or chemical properties of the bisphosphonate compounds themselves (e.g., through prodrugs).

While the use of absorption enhancers, such as ethylenediaminetetraacetic acid (EDTA), that increase intestinal permeability at high doses, has been proposed as a means of increasing absorption of oral bisphosphonates, the applicability of EDTA as an agent in human pharmacotherapy has been thought to be "impossible" in light of the effects of EDTA on mucosal integrity. Ezra et al., Adv. Drug Del. Rev. 42: 185 (2000). Still others have concluded that the high amount of EDTA required to effect an increase in GI absorption would exclude the agent as a candidate for use in oral bisphosphonate therapies. See Janner et al., Calcif. Tissue Int. 49: 280-83 (1991).

While the primary site of bisphosphonate absorption is the small intestine, bisphosphonates such as risedronate have similar absorption throughout the small intestine independent of where it was delivered. See Mitchell et al., Pharm Res., Vol. 15, No. 2: 228-232 (1998). Thus targeted delivery of the bisphosphonate alone to the small intestine would not increase absorption or efficacy of the bisphosphonate. However, others have attempted to increase the absorption of bisphosphonates by increasing the permeability of the intestinal mucosa through delivery of microparticles of chelating agents and bisphosphonate to the reported site of absorption (BR2001-006601).

Bisphosphonates such as risedronate and alendronate have been approved by a number of regulatory agencies as being effective in the treatment of various bone pathologies. However, interactions between bisphosphonates and foods and minerals (especially cations like calcium, magnesium, aluminum, and iron-containing foods or supplements) cause less of the bisphosphonate to be available for absorption. For example, in Mitchell et. al., Br. J. Clin. Pharmacol. 48: 536-542 (1999), it was demonstrated that administration of risedronate within 30 minutes of a meal reduced the amount absorbed by 50% compared to administration in the fasting state. In order to reduce this food effect, the labeling of oral bisphosphonate products instruct patients to take their medication at least thirty minutes or in the case of Ibandonate sixty minutes, before the first food of the day, and are instructed to take their calcium supplements at another time of the day, or on a day when they are not taking an oral dose of a bisphosphonate. These dosing instructions can seem complex and inconvenient to the patient, which can lead to poor patient compliance.

There is an ongoing need to develop an oral dosage form of a bisphosphonate which can be taken with or without food or beverages (i.e. has pharmaceutically effective absorption regardless of food or beverage intake), at the preference of the patient, and which does not produce upper gastrointestinal irritation.

It has been found that a pharmaceutical composition comprising a bisphosphonate, a sufficient amount of chelating agent to bind the ions and minerals in food, and a means for effecting delayed release of the bisphosphonate and the chelating agent in the lower gastrointestinal tract is useful in providing an oral dosage form which provides delivery of the bisphosphonate to the lower gastrointestinal tract, as well as pharmaceutically effective absorption of the bisphosphonate when administered with or without food or beverages. The oral dosage forms of the present invention may be taken with or without food or beverages, thus simplifying the bisphosphonate treatment therapy and leading to increased patient compliance and convenience. Further, the oral dosage forms of the invention provide for delayed release of the bisphosphonate and the chelating agent in the lower gastrointestinal tract, which may alleviate the upper gastrointestinal irritation experienced with other oral bisphosphonate dosage forms and the need to remain upright for thirty minutes post-dose administration.

SUMMARY OF THE INVENTION

The present invention relates to an oral dosage form of a bisphosphonate active ingredient comprising a safe and effective amount of a pharmaceutical composition comprising:

(a) a bisphosphonate;
(b) from about 10 mg to about 1000 mg of a chelating agent; and
(c) a delayed release mechanism to deliver the bisphosphonate and the chelating agent in the lower gastrointestinal tract.

The dosage forms of the present invention provide delivery of the bisphosphonate and the chelating agent to the lower gastrointestinal tract of the mammal subject and pharmaceutically effective absorption of the bisphosphonate active ingredient when administered with or without food or beverages.

The present invention substantially alleviates the interaction between bisphosphonates and food, which interaction results in decreased absorption of the bisphosphonate active ingredient. The resulting novel oral dosage form may thus be taken with or without food or beverages, which simplifies previously complex treatment regimens and can lead to increased patient compliance with bisphosphonate therapies and if the patients are compliant their disease can be better treated. The invention further alleviates the potential for upper gastrointestinal irritation associated with immediate release oral dosage forms of bisphosphonates, by delaying release of the bisphosphonate active ingredient until the bisphosphonate and the chelating agent reach the lower gastrointestinal tract.

The present invention further relates to a method of treating or preventing diseases characterized by abnormal calcium and phosphate metabolism comprising administering to a human or other mammal in need thereof the oral dosage form described herein.

The invention further relates to a kit comprising one or more oral dosage forms of the present invention and means for facilitating compliance with methods of this invention.

DETAILED DESCRIPTION OF THE INVENTION

Definitions and Usage of Terms

The term "bolus" as used herein means that release of a significant amount of the bisphosphonates and/or chelating agent is achieved at the site of initiation/release.

The terms "continuous" or "continuously," as used herein, mean at regular specified intervals. For example, a continuous schedule according to a dosing regimen of once weekly means that the active is given one time per week for an unspecified period of time or for as long as treatment is necessary.

The term "nutrient," as used herein, means any nutritional or dietary supplement including but not limited to vitamins, minerals, amino acids, herbs or other botanicals, or concentrates, metabolites, constituents, extracts, or combinations of the same.

The term "pharmaceutical composition," as used herein, means an oral dosage form comprised of a safe and effective amount of a bisphosphonate active ingredient and one or more pharmaceutically-acceptable excipients including at least one chelating agent. The pharmaceutical compositions described herein are comprised of from 0.5% to 75%, preferably from 1% to 40% of a bisphosphonate active ingredient and from 25% to 99.5%, preferably from 60% to 99% of pharmaceutically-acceptable excipients including at least one chelating agent.

The term "safe and effective amount," as used herein, means an amount of a compound or composition high enough to significantly positively modify the symptoms and/or condition to be treated, but low enough to avoid serious side effects (at a reasonable risk/benefit ratio), within the scope of sound medical judgment. The safe and effective amount of active ingredient for use in the method of the invention herein will vary with the particular condition being treated, the age and physical condition of the patient to be treated, the severity of the condition, the duration of the treatment, the nature of concurrent therapy, the particular active ingredient being employed, the particular pharmaceutically-acceptable excipients utilized, and like factors within the knowledge and expertise of the attending physician.

The term "sustained release" means that the bisphosphonate and/or chelating agent are not substantially released at the site of initiation but continues to be released from the initiation site throughout the remainder of the GI tract.

The term "pharmaceutically effective absorption" as used herein means an amount of a chelating compound high enough to significantly bind the metal ions and minerals in food but low enough not to significantly alter absorption of the bisphosphonate as compared to absorption in the fasted state. That is, absorption is similar with or without food. Given the high variability of bisphosphonate absorption, fed exposure within about 50% of fasting exposure is expected to be pharmaceutically effective absorption.

The term "oral dosage form," as used herein, means any pharmaceutical composition intended to be administered to the lower gastrointestinal tract of a human or other mammal via the mouth of said human or other mammal. For the purposes of the present invention, the delivered form can be in the form of a compressed tablet containing granules or particles of a bisphosphonate and a chelating agent, a capsule (e.g., soft gelatin or hard gelatin, consisting of starch, or hydroxypropylmethylcellulose) which contains beads, particles, or suspensions of the bisphosphonate and the chelating agent, or a dry mix containing granules or particles of bisphosphonate and chelating agent for making a reconstituted suspension in water (e.g., a sachet).

The term "unit dose" or "unit dosage" means a dosage form containing an amount of pharmaceutical active or nutrient suitable for administration in one single dose, according to sound medical practice. The present invention is particularly useful for the administration of unit doses in the form of tablets and capsules.

The term "gastrointestinal tract" or "GI tract," as used herein, relates to the alimentary canal, i.e., the musculo-membranous tube about thirty feet in length, extending from the mouth to the anus. The term "upper gastrointestinal tract," as used herein, means the buccal cavity, the pharynx, the esophagus, and the stomach. The term "lower gastrointestinal tract," as used herein, means the small intestine and the large intestine.

The term "small intestine," as used herein, means the part of the lower gastrointestinal tract consisting of the duodenum, the jejunum, and the ileum, i.e., that portion of the intestinal tract just distal to the duodenal sphincter of the fundus of the stomach and proximal to the large intestine.

The term "large intestine," as used herein, means the part of the lower gastrointestinal tract just distal to the small intestine, beginning with the cecum, including the ascending colon, the transverse colon, the descending colon, the sigmoid colon, and the rectum.

Bisphosphonate Active Ingredient

The terms "bisphosphonate" and "diphosphonate," as used herein, include acids, salts, esters, hydrates, polymorphs, hemihydrates, solvates, and derivatives thereof. The bisphosphonates of the present invention include those preferred compounds containing a nitrogen atom. Non-limiting examples of bisphosphonates useful herein include the following: 1-hydroxy-2-(3-pyridinyl)-ethylidene-1,1-bisphosphonic acid (risedronate) as described in U.S. Pat. No. 5,583,122, to Benedict et al., issued Dec. 10, 1996; U.S. Pat. No. 6,410,520 B2, to Cazer et al., issued Jun. 25, 2002; 4-amino-1-hydroxybutylidene-1,1-bisphosphonic acid (alendronic acid or alendronate) as described in U.S. Pat. No. 4,621,077, to Rosini et al., issued Nov. 4, 1986; U.S. Pat. No. 6,281,381 B1, to Finkelstein et al., issued Aug. 28, 2001; U.S. Pat. No. 6,008,207, to Brenner et al., issued Dec. 28, 1999; U.S. Pat. No. 5,849,726, to Brenner et al., issued Dec. 15, 1998; U.S. Pat. Pub. 2001/0021705 A1, by Brenner et al., published Sep. 13, 2001; U.S. Pat. No. 4,922,007, to Kieczykowski et al., issued May 1, 1990; U.S. Pat. No. 5,019,651, to Kieczykowski, issued May 28, 1991; 3-amino-1-hydroxypropylidene-1,1-bisphosphonic acid (pamidronate) as described in U.S. Pat. No. 4,639,338, to Stahl et al., issued Jan. 27, 1987; (4-chlorophenyl)thiomethane-1,1-diphosphonic acid (tiludronate) as described in U.S. Pat. No. 4,876,248 to Breliere et al., issued Oct. 24, 1989; 1,1-dichloromethylene-1,1-diphosphonic acid (clodronate) as described in U.S. Pat. No. 3,422,021; cycloheptylaminomethylene-1,1-bisphosphonic acid (cimadronate), as described in U.S. Pat. No. 4,970,335, to Isomura et al., issued Nov. 13, 1990; 1-hydroxy-3-(N-methyl-N-pentylamino)propylidene-1,1-bisphosphonic acid (ibandronate), which is described in U.S. Pat. No. 4,927,814, issued May 22, 1990; 1-hydroxy-2-(imidazol-1-yl)ethane-1,1-bisphosphonic acid (zoledronate); and 1-(N-phenylaminothiocarbonyl)methane-1,1-bisphosphonic acid.

In one embodiment of the invention, the bisphosphonate is selected from the group consisting of risedronate, alendronate, pamidronate, tiludronate, cimadronate, ibandronate, clodronate, zoledronate, and salts, esters, hydrates, hemihydrates, polymorphs, and solvates thereof, and combinations thereof.

It should be noted that the terms "bisphosphonate" and "bisphosphonates," as used herein in referring to the therapeutic agents of the present invention are meant to also encompass diphosphonates, biphosphonic acids, and diphosphonic acids, as well as salts, esters, hydrates, polymorphs, hemihydrates, solvates, and derivatives of these materials.

Non-limiting examples of bisphosphonate salts useful herein include those selected from the group consisting of alkali metal, alkaline metal, ammonium, and mono-, di-, tri-, or tetra-$C_1$-$C_{30}$-alkyl-substituted ammonium. Preferred salts are those selected from the group consisting of sodium, potassium, and ammonium salts.

The amount of bisphosphonate active ingredient contained in the oral dosage forms of the present invention will depend on the particular bisphosphonate selected and the continuous dosing schedule upon which the bisphosphonate is dosed to the patient. Continuous dosing schedules of daily, weekly, twice monthly, three times per month, and once monthly are non-limiting examples of dosing regimens suitable for use with the oral dosage forms of the present invention. The terms "three times per month" or "thrice monthly" mean that an oral dosage form is administered thrice, i.e., three times, during a monthly calendar period. In a thrice monthly schedule, the oral dosage forms may be administered on three consecutive days, or once about every nine to eleven days. The terms "twice per month" or "twice monthly" mean that an oral dosage form is administered twice, i.e., two times, during a monthly calendar period. In a twice monthly regimen, the oral dosage forms may be administered on consecutive days or once about every fourteen to sixteen days. The terms "monthly" or "once monthly" mean that an oral dosage form is administered once, i.e., one time during a monthly calendar period, that is, about every 28 to 31 days.

The use of a specific nomenclature in referring to the bisphosphonate or bisphosphonates is not meant to limit the scope of the present invention, unless specifically indicated. Mixed nomenclature is currently in use by those of ordinary skill in the art, for example reference to a specific weight or percentage of a bisphosphonate active ingredient is on an anhydrous monosodium salt basis for risedronate and on an anhydrous free acid basis for Alendronate. For the present invention, the phrase "about 35 mg of a bone resorption inhibiting bisphosphonate selected from the group consisting of risedronate, pharmaceutically acceptable salts thereof, and mixtures thereof, on an anhydrous monosodium salt basis" means that the amount of the bisphosphonate compound selected is calculated based on about 35 mg of anhydrous risedronate monosodium salt. The phrase "about 70 mg of a bone resorption inhibiting bisphosphonate selected from the group consisting of alendronate, pharmaceutically acceptable salts thereof, and mixtures thereof, on an anhydrous acid basis" means that the amount of the bisphosphonate compound selected is calculated based on about 70 mg of anhydrous alendronic acid.

Generally, the oral dosage forms of the present invention will contain from about 1 mg to about 500 mg of a bisphosphonate on an anhydrous weight basis. When the bisphosphonate is dosed on a daily basis, the oral dosage form contains from about 1 mg to about 100 mg bisphosphonate on an anhydrous weight basis. When the bisphosphonate is dosed on a weekly basis, the oral dosage form contains from about 10 mg to about 200 mg bisphosphonate on an anhydrous weight basis. When the bisphosphonate is dosed on a twice monthly basis, the oral dosage form contains from about 20 mg to about 300 mg bisphosphonate on an anhydrous weight basis. When the bisphosphonate is dosed three times per month, the oral dosage form contains from about 15 mg to about 250 mg bisphosphonate on an anhydrous weight basis. When the bisphosphonate is dosed on a monthly basis, the oral dosage form contains from about 50 mg to about 500 mg on an anhydrous weight basis.

When the bisphosphonate active ingredient is risedronate, a daily oral dosage form of the present invention contains from about 1 mg to about 10 mg risedronate on a risedronate anhydrous monosodium salt basis. A weekly oral dosage form contains from about 10 to about 50 mg risedronate on a risedronate anhydrous monosodium salt basis. A twice monthly oral dosage form contains from about 20 to about 100 mg risedronate, preferably about 75 mg on a risedronate anhydrous monosodium salt basis. An oral dosage form that is administered three times per month contains from about 15 to about 75 mg risedronate, preferably about 50 mg risedronate on a risedronate anhydrous monosodium salt basis. A monthly oral dosage form contains from about 50 to about 200 mg risedronate, preferably from about 100 to about 175 mg risedronate, and more preferably about 150 mg risedronate on a risedronate anhydrous monosodium salt basis.

Chelating Agent

The term "chelating agent," as used herein, means a molecule containing two or more electron donor atoms that can form coordinate bonds to a single metal ion. The term "chelating agent" is understood to include the chelating agent as well as salts thereof. For example, the term "chelating agent" includes citric acid as well as its salt forms.

The most common and widely used chelating agents coordinate to metal atoms through oxygen or nitrogen donor atoms, or both. Other less common chelating agents coordinate through sulfur in the form of —SH (thiol or mercapto) groups. After the first coordinate bond is formed, each successive donor atom that binds creates a ring containing the metal atom. A chelating agent may be bidentate, tridentate, tetradentate, etc., depending upon whether it contains two, three, four, or more donor atoms capable of binding to the metal atom. See Kirk-Othmer Encyclopedia of Chemical Technology (4th ed. 2001).

In homogeneous dilute solutions, the equilibrium constant for the formation of the complex from the solvated metal ion (e.g., calcium) and the chelating agent in its fully dissociated form is called the formation or stability constant, K. The practical significance of formation constants is that a high log K value means a large ratio of chelated to unchelated (or free) metal ion, when equivalent amounts of metal ion and chelating agent are present. Higher ratios (or difference if K is expressed in log units) of the chelating agent and the bisphosphonate complexation constants are preferred in order to have nearly all of the metal ion complexed to the chelating agent instead of the bisphosphonate. For example, for equal molar amounts of both bisphosphonate and the chelating agent, in order for the metal ions to be 99% complexed to the chelating agent, the chelating agent must have a log K which is at least 4 units higher than the bisphosphonate-metal ion complex. The other technique which can be used to favor the chelating agent-metal ion complex over that of the bisphosphonate-metal ion complex is to add a molar excess of the chelating agent which relies on the law of mass action to favor formation of the chelating agent-metal ion complex.

Although pH and solution concentration can affect the formation constant, in general, the log K of the chelating agent is preferably at least equal to that of the bisphosphonate. In other instances the log K of the chelating agent is 2 to 5 units higher than that of the bisphosphonate. In other instances, the chelating agent is present at a molar excess to that of the bisphosphonate. The chelating agent in such instances is present in at least a 2:1 molar ratio of the chelating agent to bisphosphonate.

The chelating agent may be soluble or insoluble in the gastrointestinal tract as long as it is readily available for complexation with metal ions in the food. In one instance a chelating agent that is soluble in the gastrointestinal tract is used because chelating agents that are poorly soluble may be too slowly available to complex a significant portion of the calcium in the coadministered food. In other instances the chelating agent should have a solubility comparable to or greater than that of the bisphosphonate so that it can be present in its complexing form at concentrations at least equal to that of the bisphosphonate, Various classes of chelating agents are suitable for use in the present invention. Non-limiting examples of these classes include polyphosphates (e.g., sodium tripolyphosphate, hexametaphosphoric acid, sodium acid pyrophosphate, sodium pyrophosphate, tetra sodium pyrophosphate, sodium hexametaphosphate, sodium metaphosphate); aminocarboxylic acids (e.g., ethylenediaminetetraacetic acid (EDTA), 1,2-bis(2-amino-phenoxy)ethane-N,N,N'N'-tetraacetic acid (EGTA), ethylenebis(oxyethylenenitrilo)tetraacetic acid (BAPTA), N-(hydroxyethyl)-ethylenediaminetriacetic acid (HEDTA), diethylenetriaminepentaacetic acid (DTPA), N-dihydroxyethylglycine (2-HxG), ethylenebis(hydroxyphenyl-glycine) (EHPG), glutamic acid, aspartic acid, glycine, lysine); 1,3-diketones (e.g., acetylacetone, trifluoroacetylacetone, thenoyltrifluoroacetone, ascorbic acid); hydroxycarboxylic acids (e.g., tartaric acid, citric acid, malic acid, gluconic acid, ferulic acid, lactic acid, glucuronic acid); polyamines (e.g., dietheylenetriamine, triethylenetriamine); aminoalcohols (e.g., triethanolamine, N-hydroxyethylethylene-diamine, aminoethylethanolamine (AEEA); phenols (e.g., disulfopyrocatechol, chromotropic acid); aminophenols (e.g., oxinesulfonic acid); Schiff bases (e.g., disalicylaldehyde 1,2-propylenediimine); tetrapyrroles (e.g., tetraphenylporphin, phthalocyanine); silicates (aluminum calcium silicate, calcium silicate, sodium aluminosilicate sodium calcium aluminosilicate (hydrates), tricalcium silicate); sulfur compounds (e.g., potassium ethyl xanate, sodium diethyldithiocarbamate, diethyl dithiophosphoric acid, thiourea, magnesium sulfate); synthetic macrocyclic compounds (e.g., hexamethyl-[14]-4,11-dieneN$_4$, 2.2.2-cryptate); polymers (e.g., polyethyleneimines, polymethacryloylacetone, poly(p-vinylbenzyliminodiacetic acid)), phosphonic acids (e.g., nitrilotrimethylenephosphonic acid, ethylenediaminetetra-(methylenephosphonic acid), hydroxyethylidenediphosphonic acid).

In one embodiment, the chelating agent is selected from the group consisting of EDTA, citric acid, malic acid, tartaric acid, lactic acid, adipic acid, succinic acid, aspartic acid, glutamic acid, lysine, sodium hexametaphosphate, and combinations thereof. In another embodiment, the chelating agent is EDTA, citric acid, or sodium hexametaphosphate.

In another embodiment of the invention, a monodentate chelating agent which often precipitate as metal ion complexes, may be used in place of a polydentate chelating agent. Suitable monodentate complexing agents include, but are not limited to, phosphates (e.g., sodium phosphate, sodium aluminum phosphate, sodium acid phosphate, dipotassium phosphate, disodium phosphate, monobasic) and carboxylic acids (e.g., acetic acid).

The amount of chelating agent present in the oral dosage form of the present invention will depend on the particular chelating agent or agents (i.e. mixtures of chelating agents) selected, the amount of bisphosphonate active ingredient present in the oral dosage form, and the specific portion of the lower GI tract where delivery of the chelating agent and/or bisphosphonate active ingredient is desired. After the ingestion of milk, it has been shown in the art that the concentration of calcium decreases over the length of the lower GI tract, beginning with the small intestine and proceeding through to the end of the large intestine. Mahe, J. et al., *Gastroileal nitrogen and electrolyte movements after bovine milk ingestion in humans*, Am. J. Clin. Nutr. 56: 410-16 (1992). Thus, for example, a lower concentration of a particular chelating agent may be required to effect delivery of the bisphosphonate to the transverse colon, as compared with the concentration of that same chelating agent required to effect delivery of the bisphosphonate to the terminal ileum, given the same dose of bisphosphonate active ingredient.

Generally, the oral dosage forms of the present invention will contain a safe and effective amount of a chelating agent suitable for achieving the desired chelating effect, that is, chelating the residual metal ions that are present in the gastrointestinal tract from food at the site of delivery without significantly affecting the absorption of the bisphosphonate had no food been present. In one embodiment, the oral dosage form contains from about 10 mg to about 1000 mg of a chelating agent per unit dose. In another embodiment, the oral dosage forms contain from about 10 mg to about 500 mg of a chelating agent per unit dose. When the chelating agent is disodium EDTA, the preferred range is from about 55 mg to about 500 mg, preferably from about 75 mg to about 250 mg per unit dose. When the chelating agent is citric acid, the preferred range is from about 100 mg to about 1000 mg, preferably from about 250 mg to about 500 mg per unit dose.

Delayed Release in the Lower Gastrointestinal Tract

A human or other mammal suffering from diseases or disorders involving calcium and phosphate metabolism can be successfully treated by the delivery of the bisphosphonate active ingredient to the lower GI tract of said human or other mammal. The novel dosage forms described herein effect delivery to the lower GI tract, and prohibit the undesired release of bisphosphonate in the mouth, pharynx, esophagus, and/or stomach, thereby prohibiting the erosion, ulceration, or other like irritation of the epithelial or mucosal layers of these tissues. In some instances, it may be desirable to effect delivery of the bisphosphonate and the chelating agent to the small intestine or a particular segment of the small intestine, (e.g., the terminal ileum). In other cases, it may be desirable to effect delivery of the bisphosphonate and the chelating agent to the entire lower GI tract or to a segment of the GI tract, beginning with delivery to the small intestine and continuing with delivery if needed to the large intestine. In yet other cases it may be desirable to effect a bolus delivery of the bisphosphonate and chelating agent to the lower GI or to specific segments of the lower GI tract. In one embodiment of the invention, delivery of the active beginning in the small intestine and continuing through to the large intestine may be accomplished through the use of sustained release formulations known to those skilled in the art. Such sustained release formulations are designed to slow the release of the bisphosphonate and the chelating agent over a specified time period, as the oral dose form progresses through the lower GI tract. In still other instances, it may be desirable to achieve delivery of the bisphosphonate and the chelating agent to the large intestine or a particular segment thereof (e.g., the ascending colon). In still other instances, it may be desirable to deliver the chelating agent and the bisphosphonate in a bolus amount to the large intestine. In still other instances, it may be desirable to deliver the chelating agent to one segment of the lower GI tract, and to deliver the bisphosphonate to a different segment of the lower GI tract. For example, it may be desirable to deliver the chelating agent to the terminal ileum and the bisphosphonate to the ascending colon.

The term "delayed release," as used herein, refers to a delivery of a bisphosphonate active ingredient and a chelating agent which is achieved by formulating the pharmaceutical composition comprising the bisphosphonate and the chelating agent so that their release will be accomplished at some generally predictable location in the lower GI tract more distal to that which would have been accomplished had there been no alteration in the delivery of the bisphosphonate and the chelating agent.

In another embodiment of the invention, the bisphosphonate and the chelating agent may be administered to a mammal subject by way of more than one oral dosage form, each of which comprises a means for delivering the contents of said oral dosage form to the lower GI tract. For example, a patient may take a unit dosage of a bisphosphonate, followed by a separate unit dose containing the chelating agent.

In yet another embodiment the chelant and bisphosphonate are released rapidly and as close to simultaneously as possible. This causes the local concentration of chelating agent to be higher in relationship to the metal ions in the food. The higher local concentration of chelating agent in the environment where the active is released may more effectively complex the metals in the food and facilitate absorption of the bisphosphonate. This can be conveniently achieved from a single tablet.

Various means for targeting release of the bisphosphonate and the chelating agent in the lower GI tract are suitable for use in the present invention. Non-limiting examples of means for delivery to the lower GI tract include pH triggered delivery systems, dose forms from which the release of drug is triggered by the action of bacterial enzymes, and time dependent delivery systems.

In some cases it may be desirable to initiate release of the bisphosphonate and chelating agent primary in the duodenum and/or the jejunum. In other instances it is desirable to primarily initiate release of the bisphosphonate and chelating agent in the mid-jejunum and/or the terminal ileum. In yet other cases it may be desirable to provide a sustained release of the bisphosphonate and the chelating agent primarily in the jejunum throughout the terminal ileum. For primary colonic delivery it may be desirable to initiate release of the bisphosphonate and chelating agent in the ascending and/or transverse colon.

pH Triggered Delivery Systems

One embodiment of the present invention involves coating (or otherwise encapsulating) the bisphosphonate and the chelating agent(s) with a substance which is not broken down, by the gastrointestinal fluids to release the bisphosphonate and the chelating agent until a specific desired point in the intestinal tract is reached. In one embodiment, delayed release of the pharmaceutical composition is achieved by coating the tablet, capsule, or particles, granules, or beads of the bisphosphonate and the chelating agent with a substance which is pH dependent, i.e., broken down or dissolves at a pH which is generally present in the lower GI tract, but not present in the upper GI tract (i.e., the mouth, buccal cavity, pharynx, esophagus, or stomach).

In some cases, it may be desirable that the bisphosphonate and the chelating agent are released at a particular location in the small or large intestine. In other cases, it may be desirable to release the bisphosphonate and the chelating agent independently at different locations within the lower GI tract. For example, it may be desirable to release the chelating agent in the ascending colon, and the bisphosphonate in the transverse colon. When targeted release of the bisphosphonate and the chelating agent together or separately in particular locations within the lower GI tract is desired, the selection of the coating material and/or the method of coating or otherwise combining the bisphosphonate and the chelating agent with the selected coating material or other pharmaceutically-acceptable excipients may be varied or altered as is described herein, or by any method known to one skilled in the art.

The ultimate site of and/or the rate of delivery in the lower GI tract can be satisfactorily controlled by one skilled in the art, by manipulating any one or more of the following:

(a) the active ingredient proper;
(b) the type and level of disintegrant;
(c) the type of coating, the type and level of excipients added to the coating and the concomitant desirable thickness and permeability (swelling properties) of the coating;
(d) the time dependent conditions of the coating itself and/or within the coated tablet, particle, bead, or granule;
(e) the particle size of the granulated active ingredient; and
(f) the pH dependent conditions of the coating itself and/or within the coated tablet, particle, bead, or granule.

In particular, solubility, acidity, and susceptibility to hydrolysis of the different bisphosphonate active ingredients, such as acid addition salts, salts formed with the phosphonic group (e.g., alkali metal salts, alkaline earth metal salts, etc.), and esters (e.g., alkyl, alkenyl, aryl, arylalkyl) may be used as guidelines for the proper choice. In addition, suitable pH conditions might be established within the coated tablets, particles, granules, or beads by adding a suitable buffer to the active ingredient in accordance with the desired release pattern.

Besides the above-mentioned variations in order to obtain the desired release pattern, the excipients may also be varied, as long as they do not affect the activity of the particular bisphosphonate selected.

One embodiment of the present invention is delivered to the lower GI tract utilizing a pH dependent enteric coating material made from a partly methyl esterified methacrylic acid polymer. The oral dosage form can be in the form of an enteric coated compressed tablet made of granules or particles of active ingredient or a gelatin capsule which contains beads or small particles of active ingredient which have themselves been enterically coated.

Any enteric coating which is insoluble at a pH below 5.5 (i.e., that generally found in the mouth, pharynx, esophagus, and stomach), but soluble at pH 5.5 or higher (i.e., that present in the small intestine and the large intestine) can be used in the practice of the present invention. Accordingly, when it is desired to effect delivery of the bisphosphonate and the chelating agent to the small intestine, any enteric coating is suitable which is wholly- or partially-insoluble at a pH below 5.5 and soluble at a pH 5.5 or above.

The enteric coating must be applied to the compressed tablet, the capsule (e.g., gelatin, starch, or hydroxypropylmethylcellulose) and/or the beads, particles or granules of active ingredient in a sufficient thickness so that the entire coating does not dissolve in gastrointestinal fluids at a pH below 5.5, but does dissolve at a pH of 5.5 or above. The dissolution or disintegration of the excipient coating generally does not occur until the entry of the coated dosage form into the small intestine.

It is expected that any anionic polymer exhibiting the requisite pH-dependent solubility profile can be used as an enteric coating in the practice of the present invention to achieve delivery of the bisphosphonate and chelating agent to the lower GI tract. The coating chosen must be compatible with the particular bisphosphonate active ingredient selected. The preferred polymers for use in the present invention are anionic carboxylic polymers. It is particularly preferred that the polymers are acrylic polymers, more preferably partly methyl-esterified methacrylic acid polymers, in which the ratio of free anionic carboxyl groups to ester groups is about 1:1.

A particularly suitable methacrylic acid copolymer is Eudragit L®, particularly Eudragit L 30 D-55® and Eudragit L 100-55®, manufactured by Röhm Pharma GmbH and Co. KG, Darmstadt, Germany. In Eudragit L 30 D-55®, the ratio of free carboxyl groups to ester groups is approximately 1:1. Further, said copolymer is known to be insoluble in GI fluids having a pH below 5.5, generally 1.5-5.5, i.e., that generally present in the fluid of the upper GI tract, but readily soluble at pH above 5.5, i.e., that generally present in the fluid of the lower GI tract.

Other methacrylic acid copolymer which are suitable for use in coating the oral dosage forms and/or the granules, particles, or beads of active ingredient which can be employed in the method of treatment described herein, either alone or in combination with other coatings, is Eudragit S® and Eudragit FS30D®, manufactured by Rohm Pharma GmbH and Co. KG, Darmstadt, Germany. Eudragit S® differs from Eudragit L 30 D-55®, only insofar as the ratio of free carboxyl groups to ester groups is approximately 1:2. Eudragit S® is also, like Eudragit L 30 D-55®, substantially insoluble at pH below 5.5, but unlike Eudragit L 30 D-55®, is poorly soluble in GI fluids having a pH of 5.5-7.0, such as that present in small intestinal fluids. Eudragit S® is soluble at pH 7.0 and above, i.e., that generally present in the terminal ileum and colon.

Eudragit S® can also be used alone as a coating which would provide delivery of the bisphosphonate active ingredient beginning primarily at the large intestine (more distal than the terminal ileum) via a delayed-release mechanism. In addition, Eudragit S®, being poorly soluble in intestinal fluids below pH 7.0, could be used in combination with Eudragit L 30 D-55®, soluble in intestinal fluids above pH 5.5, in order to effect a delayed release composition which could be formulated to deliver the active ingredient at various segments of the intestinal tract; the more Eudragit L 30 D-55® used, the more proximal release and delivery begins and the more Eudragit S® used, the more distal release and delivery begins.

The coating can, and usually will, contain a plasticizer and possibly other coating excipients such as coloring agents, surfactant, talc, and/or magnesium stearate, many of which are well known in the coating art. In particular, anionic carboxylic acrylic polymers usually will contain 10-25% by weight of a plasticizer, especially triethyl citrate, tributyl citrate, acteyltriethyl citrate, dibutyl phthalate, diethyl phthalate, polyethylene glycol, acetylated monoglycerides propylene glycol, and triacetin. Conventional coating techniques such as fluid-bed or pan coating are employed to apply the coating. Coating thickness must be sufficient to ensure that the oral dosage form remains essentially intact until the desired site of delivery in the lower GI tract is reached.

The solid oral dosage form may be in the form of a coated compressed tablet which contains particles or granules of the bisphosphonate active ingredient and the chelating agent, or of a soft or hard capsule (e.g., gelatin, starch, or hydroxypropylmethylcellulose), coated or uncoated, which contains beads or particles of the bisphosphonate active ingredient and the chelating agent, which themselves are enterically coated.

For sustained release of the bisphosphonate and chelating agent a sustained release polymer is required to control the dissolution rate of the bisphosphonate and chelating agent from the dosage form. If the bisphosphonate and chelating agent are both soluble (defined as 33 mg/ml or greater in water) then high levels of sustained release polymers are required. Sustained release polymers include but are not limited to hydroxypropylmethycellulose, hydroxypropylcellulose and Carbomer.

A. Enteric Coated Tablets

In one embodiment of the invention, the oral dosage form includes an enteric-coated compressed tablet. Tablets are made by combining, mixing, or otherwise adding the bisphosphonate active ingredient and the chelating agent to suitable pharmaceutical excipients including, but not limited to, sucrose, maltodextrin, lactose, cellulose, microcrystalline cellulose, talc, magnesium stearate, crospovidone, starch, and sodium starch glycolate. That mixture is then compressed into a tablet utilizing various methods known to those skilled in the art. The compressed tablet is then coated with an enteric-coating material which is made with suitable pharmaceutical excipients including, but not limited to, poly(methacrylic acid, methyl methacrylate 1:1 (Eudragit L® 100), poly(methyacrylic acid, ethyl acrylate 1:1 (Eudragit L 30 D-55®, Eudragit L 100-55®), poly(methacrylic acid, methyl methacrylate 1:2 (Eudragit S®, Eudragit F530D®), hydroxypropylmethylcellulose phthalate, cellulose acetate phthalate, polyvinyl acetate phthalate, shellac, cellulose acetate succinate, cellulose acetate trimellatate, polyethylene glycol 400-8000, triacetin, dibutyl phthalate, acetylated monoglycerides, triethyl citrate, talc, and iron oxide. The enteric-coating material is then applied to the compressed tablet utilizing numerous spraying techniques available to those skilled in the art.

The enteric-coating of the tablets is not soluble in the fluids of the mouth, pharynx, esophagus, or stomach, and thereby prohibits the release of the bisphosphonate and the EDTA until oral dosage form reaches the lower GI tract. For the coating method described herein using methacrylate copolymers, when the desired site of delivery is the lower GI tract, it has been found that a coating thickness of between about 10 and about 500 microns usually is required. In one embodiment of the invention, the thickness is between about 10-30 and about 50 microns. In another embodiment, the thickness is between about 200 and about 350 microns. Another way to characterize the coating is to express the amount of coating as weight gain or coating solids relative to the original tablet weight. In one embodiment of the invention the weight gain of coating solids is 5-50% of the original tablet weight, in another embodiment the coating solids weight gain is 5-15%, in yet another embodiment it is 15-30% and in another it is 30-50%

B. Enteric-Coated Beads or Granules

Another oral dosage form suitable for use in the present invention consists of gelatin or starch capsules which contain enteric-coated beads or granules of the active ingredient. The gelatin or starch capsules may themselves be enteric-coated, if desired. The use of capsules which contain enteric coated beads is generally not preferred from a standpoint of manufacturing cost and difficulty. However, some active ingredients which must be given in relatively higher doses are sometimes difficult to compress into tablets. In addition, when ingested with food, tablets often sit in the stomach until the digestion of food causes the opening of the pyloric sphincter and pushes the tablet into the duodenum. When uncoated gelatin or starch capsules are used, the gelatin or starch will break down in the stomach, releasing the enteric coated beads. The beads can travel through the pylorus independently of the presence of food, and there is decreased risk of large amounts of the active ingredient sitting for any period of time in direct contact with the epithelial and mucosal tissues. As used herein, "beads" refers to particles containing the active ingredient which are prepared by applying the bisphosphonate active ingredient and the chelating agent to inert substrate spheres, or beads, preferably using a polymer film.

The substrate bead, accordingly, is used as an inert substrate to which the bisphosphonate and the chelating agent are applied. The beads may be made from one, or a mixture of, a group selected from, but not limited to, sucrose, mannitol, lactose, dextrose, sorbitol, cellulose, and starch, preferably sucrose and starch. In one embodiment of the invention, the size of the inert substrate beads is in the range of from 0.25 mm to 7.00 mm, preferably from 1.00 mm to 4.00 mm. In addition, suitable inert substrate beads may be purchased, as pre-prepared, for example, non-pareil PG beads, manufactured by Penwest, Patterson, N.Y.

The bisphosphonate active ingredient and the chelating agent must be affixed to the inert substrate beads. In one embodiment, the active ingredient and the chelating agent are affixed using a polymer film. In addition, if an active ingredient is chosen that is deliquescent, the polymer film will serve to prevent the active from picking up moisture. If the active ingredient chosen is unstable in any way, the polymer film may provide some stability. The polymer film preferably comprises a mixture of hydroxypropylmethylcellulose, ethylcellulose, polyvinylpyrrolidone, and/or hydroxypropylcellulose; and a suitable plasticizer. Plasticizers suitable for use in the film include, but are not limited to, polyethylene glycol, propylene glycol, triacetin, acetylated monoglycerides, phthalate esters, castor oil, dibutyl secabate, triethyl citrate, and selected mixtures thereof. In one embodiment, the plasticizer comprises from 5% to 40% of the polymer film, preferably from 10% to 25% of the polymer film.

The polymer film may further comprise optional fillers, pigments, and dyes as described hereinabove.

The polymer or polymer mix can include any combination that offers protection against moisture pickup and/or oxygen transfer, and which is designed for immediate release of the active ingredient by intestinal fluid. The amount of bisphosphonate to be applied to the inert substrate beads may vary depending on the concentration desired in the finished product. However, the weight of the applied film on the substrate bead is between about 5-50% weight gain, preferably between 5-25% weight gain. The term "weight gain," as used herein, means the weight increase as a percentage of the amount of applied solids to the substrate.

After the inert substrate beads are coated with the active ingredient and chelating agent, they must be enterically coated. The enteric coating is applied using various spray techniques known to one skilled in the art. The coating is applied to the beads of active ingredient at a thickness of about 20-350 microns, in another embodiment about 30-100 microns. The coating amount can be characterized as a weight gain of about 10-75%, in other cases about 20-50% relative to the original weight of the beads.

It may be desired to coat the granules of the bisphosphonate active ingredient and the chelating agent instead of spraying inert substrate beads with the bisphosphonate and the chelating agent. "Granules," as used herein, means particles of active ingredient and chelating agent in combination with suitable pharmaceutically-acceptable excipients as described hereinabove. Although it is preferable to encapsulate the enteric-coated granules using starch or gelatin capsules, for administration as an oral dosage form, the granules may also be compressed into tablets.

Granules can be obtained by extrusion of a moist kneaded mass followed by spheronization and drying. Granules with a regular molding are preferred, for example, rod-shaped, cylindrical, or spherical. In one embodiment, the granules are spherical pellet-type granules, with a diameter between about 0.3 and about 1.5 mm, preferably between about 0.5 and about 1.25 mm.

Suitable pharmaceutically-acceptable excipients for making the granules to be used in the novel dosage forms described herein include, but are not limited to, lactose, mannitol, cellulose, sucrose, and starch.

The prepared granules of active ingredient and chelating agent are then coated with an enteric coating material prepared from the pharmaceutically-acceptable excipients, using various coating techniques known to those skilled in the art. The coating is applied to the granules at a thickness of about 20-350 microns, preferably about 30-100 microns. The coating amount can be characterized as a weight gain of about 10-75%, preferably about 20-50% relative to the original weight of the beads.

Bacterial Enzyme Triggered Systems

In one embodiment of the invention, delivery of the bisphosphonate and the chelating agent to the lower GI tract is achieved through the use of a bacterial enzyme triggered system. Oral dosage forms from which drug release is triggered by the action of bacterial enzymes in the colon are known in the art. Various approaches to bacterially-triggered delivery systems suitable for use in the present invention include disulfide polymers, glycosidic prodrugs, and polysaccharides as matrices/coating agents. Watts, Peter J. & Illum, Lisbeth, Drug Dev. and Indus. Pharm., 23(9): 893-917 (1997).

Further approaches to bacterially-triggered delivery systems suitable for use are disclosed in Katsuma et al., J. of Pharm. Sci. 93(5): 1287-99 (2004). In one embodiment of the invention, the colon-targeted delivery system CODES™ (Yamanouchi Pharma Technologies, Norman, Okla.) is used to deliver the bisphosphonate and the chelating agent to the colon. This system comprises a tablet core containing a bisphosphonate, a chelating agent, and a saccharide, which tablet core is coated with an acid soluble material, such as Eudragit E®, and then coated with an enteric coating, such as Eudragit L®. The enteric coating protects the dosage form from degradation in the stomach, and is subsequently dissolved in the small intestine following gastric emptying. The acid-soluble coating protects against degradation as the dosage form travels through the small intestine. When the dosage form reaches the large intestine, local microflora ferment the saccharide in the tablet core into short chain fatty acids, which then dissolve the acid-soluble coating to release the core tablet contents in the colon.

Suitable enteric coating materials include Eudragit L-100®, Eudragit S®, Eudragit L 30 D-55®, Eudragit F530D® cellulose acetate phthalate, shellac, or any enteric coating material that dissolves above pH 5.5. The enteric coating is applied using various spray techniques known to one skilled in the art. The enteric coating may further comprise one or more pharmaceutically-acceptable excipients including, but not limited to, talc, triethyl citrate, polyethylene glycol, Tween 80® (polyoxyethylene sorbitan monooleate, available from Sigma Chemical CO., St. Louis, Mo.), castor oil. The enteric coating is applied to the tablet core coated in acid-soluble material to provide a weight gain of 2.5% to 40%.

Suitable acid-soluble coating materials include those materials which dissolve at a pH less than 6.0, including but not limited to Eudragit E-100®, polyvinyl acetyl diethylaminoacetate, and chitosan. The acid-soluble coating may further comprise one or more pharmaceutically-acceptable excipients. Such excipients include, but are not limited to, hydroxypropylmethylcellulose, Eudragit RS®, ethylcellulose, hydroxypropylcellulose, polyethylene oxide, polyvinylpyrrolidone, triacetin, polyethylene glycol 400, triethylcitrate, Tween 80®, and castor oil. The acid-soluble coating is applied using various spray techniques known to one skilled in the art. The coating is applied to the tablet core at a weight gain of 2.5% to 40%.

The tablet core comprises one or more saccharide in an amount of 10% to 99.9% by weight of the tablet. The action of enterobacteria in the lower GI tract causes the saccharide(s) to be degraded into shorter chain fatty acids, which then dissolve the acid-soluble coating. Suitable saccharides include, but are not limited to, lactulose, raffinose, cellobiose, stachyose, fructoligosaccharide, sucrose, glucose, xylose, fructose, maltose, galactose cellulosic, and combinations thereof.

The tablet core comprises a bisphosphonate active ingredient, a chelating agent, and may contain one or more pharmaceutically-acceptable excipients. Suitable excipients include, but are not limited to, crystalline cellulose, calcium hydrogen phosphate, polyvinylpyrrolidone, magnesium stearate, sucrose, starch, magnesium oxide, and sodium lauryl sulfate.

Time Dependent Delivery Systems

In another embodiment of the invention, delivery of the bisphosphonate and the chelating agent to the lower GI tract is achieved through the use of a time dependent delivery system. Given established transit times after gastric emptying, drug and/or chelating agent release can be targeted to the various segments of the lower GI tract. For example, in order to target release of the bisphosphonate active ingredient and the chelating agent to the colon, release should be delayed until 3-4 hours after leaving the stomach. Watts, Peter J. & Illum, Lisbeth, Drug Dev. and Indus. Pharm., 23(9): 893-917 (1997). Approaches to time dependent delivery systems suitable for use in the present invention include, but are not limited to, such devices as the Pulsincap™ (Scherer DDS, Strathclyde, U.K.), the Time Clock™ (Zambon Group, Milan, Italy), and SyncroDose™ (Penwest, Patterson, N.Y.), as well as various coatings which degrade over time to release tablet contents such as hydroxypropylmethylcellulose, hydroxypropylcellulose, or any suitable hydrogel.

In one embodiment of the invention, the time-dependent device Pulsincap™ is used to target delivery of the active ingredient and the chelating agent to the lower GI tract. The active ingredient and other excipients, including the chelating agent, are contained inside the Pulsincap™ water-insoluble capsule by means of a hydrogel plug which is covered by a water-soluble cap. The entire dose form is optionally coated in an enteric-coating material to protect the dose form from degradation while in transit through the upper GI tract. When the patient swallows the Pulsincap™ dosage form, the water-soluble cap dissolves and exposes the hydrogel plug to gastric and/or intestinal fluids. The hydrogel cap then swells, and eventually pops out of the capsule body, thus releasing the capsule contents. Release of the capsule contents can be targeted to specific regions of the lower GI tract by modifying the hydrogel plug properties. Watts, Peter J. & Illum, Lisbeth, Drug Dev. and Indus. Pharm., 23(9): 893-917 (1997).

In one embodiment of the invention, a time dependent coating is applied over a compressed tablet and then an enteric coating is applied over the time dependent coating. This is used to target delivery of the active ingredient and the chelating agent to the lower GI tract. The active ingredient and other excipients, including the chelating agent, are contained inside the core tablet. The entire dose form is coated with a time dependent coating and then an enteric coating. The enteric-coating material is to protect the dose form from degradation while in transit through the upper GI tract. When the patient swallows the dosage form the enteric coating dissolves after the dosage form leaves the stomach and then the core tablet starts to swell. Eventually, at a predetermined time in the lower GI tract fluids, the time dependent coating will rupture and releases the contents of the core tablet in the lower GI tract. Release of the core tablet contents can be targeted to specific regions of the lower GI tract by modifying the core tablet, time dependent coating and/or the enteric coating.

Pharmaceutically-Acceptable Excipients

Pharmaceutically-acceptable excipients include, but are not limited to, polymers, resins, plasticizers, fillers, lubricants, diluents, binders, disintegrants, solvents, co-solvents, surfactants, buffer systems, preservatives, sweetener agents, flavoring agents, pharmaceutical-grade dyes or pigments, chelating agents, viscosity agents, and combinations thereof. Pharmaceutically-acceptable excipients can be used in any component in making the oral dosage form, i.e. core tablet or coating.

Flavoring agents and dyes and pigments among those useful herein include but are not limited to those described in Handbook of Pharmaceutical Excipients (4th Ed., Pharmaceutical Press 2003).

Suitable co-solvents include, but are not limited to, ethanol, isopropanol, and acetone.

Suitable surfactants include, but are not limited to, polyoxyethylene sorbitan fatty acid esters, polyoxyethylene monoalkyl ethers, sucrose monoesters, simethicone emulsion, sodium lauryl sulfate, Tween 80®, and lanolin esters and ethers.

Suitable preservatives include, but are not limited to, phenol, alkyl esters of parahydroxybenzoic acid, benzoic acid and the salts thereof, boric acid and the salts thereof, sorbic acid and the salts thereof, chlorbutanol, benzyl alcohol, thimerosal, phenylmercuric acetate and nitrate, nitromersol, benzalkonium chloride, cetylpyridinium chloride, methyl paraben, and propyl paraben.

Suitable fillers include, but are not limited to, starch, lactose, sucrose, maltodextrin, and microcrystalline cellulose.

Suitable plasticizers include, but are not limited to, triethyl citrate, polyethylene glycol, propylene glycol, dibutyl phthalate, castor oil, acetylated monoglycerides, and triacetin.

Suitable polymers include, but are not limited to, ethylcellulose, cellulose acetate trimellitate, hydroxypropylmethylcellulose phthalate, cellulose acetate phthalate, polyvinyl acetate phthalate, and Eudragit® L 30-D, Eudragit® L 100-55, Eudragit® F530D and Eudragit® S 100 (Röhm Pharma GmbH and Co. KG, Darmstadt, Germany), and Acryl-EZE® and Sureteric® (Colorcon, Inc., West Point, Pa.).

Suitable lubricants include, but are not limited to, magnesium stearate, stearic acid, and talc.

Methods of Use

The present invention further relates to a method of treating or preventing diseases characterized by abnormal calcium and phosphate metabolism comprising administering to a human or other mammal in need thereof a safe and effective amount of a pharmaceutical composition delivered to said human or other mammal via the oral dosage forms described herein.

Diseases characterized by abnormal calcium and phosphate metabolism include, but are not limited to, osteoporosis, Paget's disease (osteitis deformans), hyperparathyroidism, hypercalcemia of malignancy, osteolytic bone metastasis, myositis ossificans progressiva, calcinosis universalis, and such afflictions as arthritis, neuritis, bursitis, tendonitis, and other inflammatory conditions which predispose involved tissue to deposition of calcium phosphates.

The oral dosage forms of the present invention are suitable for administration to a patient according to a continuous dosing interval of daily, weekly, three times per month, twice monthly, and monthly.

Kits

The present invention further comprises kits that are particularly useful for administering the oral dosage forms described herein according to a continuous dosing schedule of daily, weekly, three times per month, twice monthly, or monthly. Such kits comprise one or more oral dosage forms comprising a bisphosphonate and a chelating agent and a means for facilitating compliance with methods of this invention. Such kits provide a convenient and effective means for assuring that the subject to be treated takes the appropriate oral dosage form in the correct dosage and in the correct manner. The compliance means of such kits includes any means which facilitates administering the active according to a method of this invention. Such compliance means includes instructions, packaging, and dispensing means, and combinations thereof. The kits can also comprise a means for aiding the memory, including but not limited to a listing of the days of the week, numbering, illustrations, arrows, Braille, calendar stickers, reminder cards, or other means specifically selected by the patient. Examples of packaging and dispensing means are well known in the art, including those described in U.S. Pat. No. 4,761,406, Flora et al., issued Aug. 2, 1988; and U.S. Pat. No. 4,812,311, Uchtman, issued Mar. 14, 1989.

Optionally, the kits can comprise at least one oral dosage form comprising a bisphosphonate and a chelating agent and at least one oral dosage form of an accompanying nutrient. Preferred nutrients are calcium and/or vitamin D. Oral forms of calcium suitable for use in the present invention include capsules, compressed tablets, chewable tablets, and the like. Typical salt forms of calcium suitable for use in the present invention include but are not limited to calcium carbonate, calcium citrate, calcium malate, calcium citrate malate, calcium glubionate, calcium gluceptate, calcium gluconate, calcium lactate, dibasic calcium phosphate, and tribasic calcium phosphate. In one embodiment, kits of the present invention may include tablets comprising 400 mg to 1500 mg calcium.

The term "vitamin D," as used herein, refers to any form of vitamin D that may be administered to a mammal as a nutrient. Vitamin D is metabolized in the body to provide what is often referred to as "activated" forms of vitamin D. The term "vitamin D" can include activated and non-activated forms of vitamin D, as well as precursors and metabolites of such forms. Precursors of these activated forms include vitamin $D_2$ (ergocalciferol, produced in plants) and vitamin $D_3$ (cholecalciferol, produced in skin and found in animal sources and used to fortify foods). Vitamins $D_2$ and $D_3$ have similar biological efficacy in humans. Non-activated metabolites of vitamins $D_2$ and $D_3$ include hydroxylated forms of vitamins $D_2$ and $D_3$. Activated vitamin D analogs cannot be administered in large doses on an intermittent schedule, due to their toxicity in mammals. However, non-activated vitamin $D_2$, vitamin $D_3$, and their metabolites may be administered in larger doses than "active" forms of vitamin D on an intermittent basis, without toxicity. In one embodiment, kits of the present invention may include tablets comprising 100 IU to 10,000 IU of vitamin D.

In another embodiment, kits of the present invention may include one or more nutrient tablets comprising both calcium and vitamin D. In a further embodiment, the unit dose of nutrient comprises about 600 mg calcium and about 400 IU vitamin D.

The following non-limiting examples illustrate the formulations, processes, and uses of the present invention.

EXAMPLES

Example I

Enteric-Coated Tablets Containing Risedronate and EDTA

Enteric-coated tablets containing risedronate and EDTA are made by preparing a coating composition and compressed tablets containing risedronate and EDTA, and then applying said coating composition to said tablets.

An enteric coating composition is prepared in the form of a lacquer containing the following excipients, per tablet:

A. Enteric Coating Suspension
Ingredients:

| Eudragit L 30 D-55 ® (wet basis) (manufactured by Röhm Pharma GmbH and Co. KG, Darmstadt, Germany) | 143.3 mg |
|---|---|
| Triethylcitrate | 6.45 mg |
| Talc | 21.5 mg |
| Red Iron Oxide | 0.22 mg |
| Simethicone emulsion (30%) | 0.43 mg |
| Polysorbate 80 | 0.43 mg |
| Purified Water | 307.7 mg |

The enteric coating is prepared using the following method:

A pigment suspension is prepared by adding polysorbate 80, ground ferric oxide, and talc to approximately two-thirds of the purified water while mixing. The suspension is mixed for at least two hours. The 30% simethicone emulsion and the remaining water are added to the pigment suspension and mixed for at least 45 minutes. The Eudragit L 30 D-55 solution and triethyl citrate are combined and mixed for at least 45 minutes. The pigment suspension is then added to the Eudragit solution and mixed for 30 to 60 minutes. The resulting coating suspension is screened and mixed throughout the coating process. The core tablets are transferred to the coating pan and preheated with occasional jogging. Tablets are coated, using a typical pan coating process until the required quantity of coating solution has been applied. Tablets are then cooled and collected in suitable containers.

A coating weight gain of 30% (total solids) is applied by spraying the above composition onto compressed tablets containing risedronate and EDTA, prepared in Part B below.

B. Compressed Tablets Containing Risedronate and EDTA

The enteric coating suspension prepared in Part A above is sprayed onto 35 mg risedronate tablets, each tablet weighing 240 mg and each containing:

Active Ingredients:

| Risedronate Sodium Chelant: | 35 mg* |
|---|---|
| Disodium EDTA Excipients: | 100 mg |
| Microcrystalline cellulose | 85.8 mg |
| Sodium starch glycolate | 6 mg |
| Stearic acid | 12 mg |
| Magnesium stearate | 1.2 mg |

*This amount is calculated on a risedronate anhydrous monosodium salt basis.

Tablets having the composition set forth above are prepared as follows:

The risedronate sodium, edetate disodium, sodium starch glycolate, and microcrystalline cellulose are passed through a mill and added to a blender equipped with an intensifier bar. The mixture is blended for approximately ten minutes with the intensifier bar on. The stearic acid and magnesium stearate are screened and added to the blender. The blend is mixed for approximately 3 minutes with the intensifier bar off. The blend is compressed into tablets using a suitable tablet press.

Example II

Enteric-Coated Tablets Containing Risedronate and EDTA

Enteric-coated tablets containing risedronate sodium are prepared as described below, using a similar method set forth in Example I.

A coating composition is prepared from a lacquer containing the following excipients, per tablet:

Ingredients:

| Acryl-EZE (manufactured by 200 mg Colorcon, Inc., West Point, Pa.) dry solids | 200 mg |
|---|---|
| Purified Water | 950 mg |

A coating weight of 40% weight gain is applied by conventional pan coating to tablets containing 150 mg risedronate and 75 mg EDTA so that oval tablets, each weighing 500 mg, result. The composition of each tablet is as follows:

Active Ingredients:

| Risedronate Sodium Chelant: | 150 mg* |
|---|---|
| Disodium EDTA Excipients: | 75 mg |
| Mannitol | 100 mg |
| Starch 1500 | 159 mg |
| Silicon Dioxide | 1 mg |
| Stearic acid | 15 mg |

*This amount is calculated on a risedronate anhydrous monosodium salt basis.

Example III

Enteric-Coated Tablets Containing Risedronate and EDTA

Enteric-coated tablets containing risedronate and EDTA are made by preparing a coating composition and compressed tablets containing risedronate and EDTA, and then applying said coating composition to said tablets.

An enteric coating composition is prepared in the form of a lacquer containing the following excipients, per tablet:

A. Enteric Coating Suspension
Ingredients:

| | |
|---|---|
| Eudragit L 30 D-55 ® (wet basis) (manufactured by Röhm Pharma GmbH and Co. KG, Darmstadt, Germany) | 47.8 mg |
| Triethylcitrate | 2.15 mg |
| Talc | 7.17 mg |
| Red Iron Oxide | 0.07 mg |
| Simethicone emulsion (30%) | 0.14 mg |
| Polysorbate 80 | 0.14 mg |
| Purified Water | 102.6 mg |

The enteric coating is prepared using the following method:

A pigment suspension is prepared by adding polysorbate 80, ground ferric oxide, and talc to approximately two-thirds of the purified water while mixing. The suspension is mixed for at least two hours. The 30% simethicone emulsion and the remaining water are added to the pigment suspension and mixed for at least 45 minutes. The Eudragit L 30 D-55 solution and triethyl citrate are combined and mixed for at least 45 minutes. The pigment suspension is then added to the Eudragit solution and mixed for 30 to 60 minutes. The resulting coating suspension is screened and mixed throughout the coating process. The core tablets are transferred to the coating pan and preheated with occasional jogging. Tablets are coated, using a typical pan coating process until the required quantity of coating solution has been applied. Tablets are then cooled and collected in suitable containers.

A coating weight gain of 10% (total solids) is applied by spraying the above composition onto compressed tablets containing risedronate and EDTA, prepared in Part B below.

B. Compressed Tablets Containing Risedronate and EDTA

The enteric coating suspension prepared in Part A above is sprayed onto 35 mg risedronate tablets, each tablet weighing 230 mg and each containing:

Active Ingredients:

| | |
|---|---|
| Risedronate Sodium | 35 mg* |
| Chelant: | |
| Disodium EDTA | 100 mg |
| Excipients: | |
| Microcrystalline cellulose | 25.8 mg |
| Hypromellose | 76.8 mg |
| Magnesium stearate | 2.4 mg |

*This amount is calculated on a risedronate anhydrous monosodium salt basis.

Tablets having the composition set forth above are prepared as follows:

The risedronate sodium, edetate disodium, hypromellose, and microcrystalline cellulose are passed through a mill and added to a blender equipped with an intensifier bar. The mixture is blended for approximately twenty minutes with the intensifier bar on. Approximately 50% of the magnesium stearate is screened and added to the blender. The blend is mixed for approximately 3 minutes with the intensifier bar off and then chilsonated and milled. The remaining magnesium stearate is screened and added to the blender with the granulation. The blend is mixed for approximately 3 minutes with the intensifier bar off. The blend is compressed into tablets using a suitable tablet press.

Example IV

Enteric-Coated Tablets Containing Risedronate and EDTA

Enteric-coated tablets containing risedronate and EDTA are made by preparing a coating composition and compressed tablets containing risedronate and EDTA, and then applying said coating composition to said tablets.

An enteric coating composition is prepared in the form of a lacquer containing the following excipients, per tablet:

A. Enteric Coating Suspension
Ingredients:

| | |
|---|---|
| Eudragit L 30 D-55 ® (wet basis) (manufactured by Röhm Pharma GmbH and Co. KG, Darmstadt, Germany) | 150 mg |
| Triethylcitrate | 10 mg |
| Talc | 30 mg |
| Black Iron Oxide | 0.1 mg |
| Purified Water | 250 mg |

The enteric coating is prepared using the following method:

The talc and black iron oxide are added to a portion of purified water and mixed until uniform. The triethylcitrate is added with continuous mixing. The resulting pigment suspension is next passed through a screen or a suitable mill to break up agglomerates. The Eudragit L 30 D-55® is screened and then added to a suitable vessel and diluted with a portion of the purified water. The pigment suspension is then added to the diluted Eudragit suspension and mixed until uniform.

In a suitable coating pan, the compressed tablets (10 kg) containing risedronate and EDTA, described below, are warmed to about 30-35° C. The enteric coating suspension is sprayed onto the tablets at approximately 30 grams per minute. When the spray cycle is completed, the temperature is reduced and the tablets are removed and dried at 30-35° C. for approximately 1 hour.

A coating weight gain of 35% (total solids) is applied by spraying the above composition onto compressed tablets containing risedronate and EDTA, prepared in Part B below.

B. Compressed Tablets Containing Risedronate and EDTA

The enteric coating suspension prepared in Part A above is sprayed onto 5 mg risedronate tablets, each tablet weighing 240 mg and each containing:

Active Ingredients:

| | |
|---|---|
| Risedronate sodium | 5.0 mg* |
| Chelant: | |
| Disodium EDTA | 75.0 mg |

-continued

| Excipients: | |
|---|---|
| Microcrystalline cellulose | 149.5 mg |
| Sodium starch glycolate | 9 mg |
| Stearic acid | 1.5 mg |

*This amount is calculated on a risedronate anhydrous monosodium salt basis.

Tablets having the composition set forth above are prepared as follows:

The tablets are prepared by sieving the risedronate active ingredient and the EDTA with ½ of the microcrystalline cellulose into a twin shell blender. The blend is then mixed until uniform. Then, ½ of the stearic acid is added and the blend is mixed further. The blend is then roller compacted and milled. The remaining microcrystalline cellulose and sodium starch glycolate are added and mixed until uniform. The remaining stearic acid is then added and mixed until adequate lubrication is achieved. Tablets are then compressed on a rotary tablet press.

Example V

Capsules Containing Enteric-Coated Particles

Capsules containing enteric-coated particles are made by preparing particles of the risedronate sodium active ingredients and EDTA, and then encapsulating them into a gelatin capsule. The particles have the following composition:

| Component | mg/capsule |
|---|---|
| Active Ingredients: | |
| Risedronate Sodium | 35 mg* |
| Chelant: | |
| EDTA | 75 mg |
| Excipients: | |
| Lactose | 50 mg |
| Microcrystalline Cellulose | 50 mg |

*This amount is calculated on a risedronate anhydrous monosodium salt basis.

A mixture of risedronate sodium, EDTA, lactose, and microcrystalline cellulose is moistened with water and kneaded, extruded, and spheronized. The dried particles are subsequently coated with enteric coating material prepared as described in Example XIII.

The enteric coating has the following composition:

| Component | mg/capsule |
|---|---|
| Eudragit L 30 D-55 ® | 90 |
| Triethylcitrate | 6 |
| Antifoam AF | 2 |
| Talc | 7 |
| Water | 275 |

The particles having the composition described above are coated in a coating column with a coating mixture having the above composition.

The enteric coating is prepared utilizing the procedure set forth in Example XIII. In a suitable coating column, the particles are warmed to about 25° C. and enteric coating solution is applied to the particles by spraying a coating of 20% weight gain to the particles. When the spray cycle is completed, the air is turned off and the particles are cooled to room temperature.

The lacquered particles are powdered with talc and encapsulated using capsules (capsule size 0), with a commercial capsule filling machine.

Example VI

Bacterial Enzyme Triggered Tablets Containing Risedronate and Sodium Hexametaphosphate Bacterial enzyme triggered tablets containing risedronate and sodium hexametaphosphate are made by preparing a two layer coating composition and compressed tablets containing risedronate and sodium hexametaphospahte and then applying said coating composition to said tablets.

The first layer (Acid Soluble Coating Layer) coating composition is prepared in the form of a lacquer containing the following excipients, per tablet:

A. Acid Soluble Coating Layer
Ingredients:

| | |
|---|---|
| Eudragit E 100 ® | 40.0 mg |
| (manufactured by Röhm Pharma GmbH and Co. KG, Darmstadt, Germany) | |
| Hydroxypropylmethylcellulose | 10 mg |
| Talc | 10 mg |
| Ethanol | 450 mL |
| Purified Water | 50 mL |

The acid soluble coating is prepared using the following method:

A talc suspension is prepared by adding talc to approximately one-third of the purified water while mixing. The suspension is mixed for at least two hours. The Eudragit E 100® and hydroxyproylmethylcelluse are added to the remaining water and ethanol mixture and mixed until dissolved. The talc suspension is then added to the Eudragit solution and mixed for 30 to 60 minutes. The resulting coating suspension is screened and mixed throughout the coating process.

B. Enteric Coating Suspension (Second Layer)
Ingredients:

| | |
|---|---|
| Eudragit L 30 D-55 ® (wet basis) | 150 mg |
| (manufactured by Röhm Pharma GmbH and Co. KG, Darmstadt, Germany) | |
| Triethyl citrate | 6.0 mg |
| Talc | 15.0 mg |
| Red Iron Oxide | 0.25 mg |
| Purified Water | 260 mg |

The enteric coating is prepared using the following method:

A pigment suspension is prepared by adding ground ferric oxide, and talc to approximately two-thirds of the purified water while mixing. The suspension is mixed for at least two hours. The Eudragit L 30 D-55 solution and triethyl citrate are combined and mixed for at least 45 minutes. The pigment suspension is then added to the Eudragit solution and mixed for 30 to 60 minutes. The resulting coating suspension is screened and mixed throughout the coating process.

The compressed tablets as described below are transferred to the coating pan and preheated with occasional jogging. The compressed tablets are coated with the Acid Soluble Coating then with the Enteric Coating Suspension using a typical pan coating process until the required quantity of coating solution has been applied. Tablets are then cooled and collected in suitable containers.

A coating weight gain of 12% for the Acid Soluble Coating and 13% for the Enteric Coating (total solids compared to that of the core tablet weight) is applied by spraying the above composition (A and B) onto compressed tablets containing risedronate and sodium hexametaphosphate prepared in Part C below.

C. Compressed Tablets Containing Risedronate and Sodium Hexametaphosphate

The Acid Soluble Coating and the Enteric Coating suspension prepared in Part A and B above is sprayed onto 35 mg risedronate tablets, each tablet weighing 500 mg and each containing:

Active Ingredients:

| Risedronate Sodium | 35 mg* |
|---|---|
| Chelant: | |
| Sodium hexametaphosphate | 150 mg |
| Excipients: | |
| Lactulose | 300 mg |
| Stearic acid | 14.5 mg |
| Magnesium stearate | 0.5 mg |
| Purified Water | 100.0 mg |

*This amount is calculated on a risedronate anhydrous monosodium salt basis.

Tablets having the composition set forth above are prepared as follows:

The risedronate sodium, sodium hexametaphosphate, lactulose and the stearic acid are passed through a mill and added to a blender equipped with an intensifier bar. The mixture is blended for approximately ten minutes with the intensifier bar on and granulated with the purifed water for 15 minutes. The mixture is dried overnight at 30° C., passed through a mill. The magnesium stearate is screened and added to the blender. The blend is mixed for approximately 3 minutes. The blend is compressed into tablets using a suitable tablet press.

Example VII

Time Dependent and Enteric Coated Tablets Containing Risedronate and Sodium Citrate Time Dependent and Enteric Tablets containing risedronate and sodium citrate are made by preparing a two layer coating composition and compressed tablets containing risedronate and sodium citrate and then applying said coating composition to said tablets.

The first layer (Time Dependent Coating Layer) coating composition is prepared in the form of a polymer containing the following excipients, per tablet:

A. Acid Soluble Coating Layer

Ingredients:

| Ethylcellulose | 40.0 mg |
|---|---|
| Dibuty Sebacate | 8 mg |
| Toluene | 250 mg |
| Ethyl Alcohol | 70 mg |

The acid soluble coating is prepared using the following method:

A solution is prepared by adding the ethylcellulose to approximately two-thirds of the toluene:ethyl alcohol mixture while mixing. The solution is mixed for at least two hours. The dibuty sebacate is added and mixed for an additional two hours. The resulting coating solution is screened and mixed throughout the coating process.

B. Enteric Coating Suspension

Ingredients:

| Eudragit L 30 D-55 ® (wet basis) (manufactured by Röhm Pharma GmbH and Co. KG, Darmstadt, Germany) | 150 mg |
|---|---|
| Triethyl citrate | 6.0 mg |
| Talc | 15.0 mg |
| Red Iron Oxide | 0.25 mg |
| Purified Water | 260 mg |

The enteric coating is prepared using the following method:

A pigment suspension is prepared by adding ground ferric oxide, and talc to approximately two-thirds of the purified water while mixing. The suspension is mixed for at least two hours. The Eudragit L 30 D-55 solution and triethyl citrate are combined and mixed for at least 45 minutes. The pigment suspension is then added to the Eudragit solution and mixed for 30 to 60 minutes. The resulting coating suspension is screened and mixed throughout the coating process.

The compressed tablets are transferred to the coating pan and preheated with occasional jogging. The compressed tablets are coated with the Time Dependent Coating then with the Enteric Coating Suspension using a typical pan coating process until the required quantity of coating solution has been applied. Tablets are then cooled and collected in suitable containers.

A coating weight gain of 10% for the Time Dependent Coating and 13% Enteric Coating (total solids compared to that of the core tablet weight) is applied by spraying the above composition (A and B) onto compressed tablets containing risedronate and sodium citrate prepared in Part C below.

C. Compressed Tablets Containing Risedronate and Sodium Citrate

The Acid Soluble Coating and the Enteric Coating suspension prepared in Part A and B above is sprayed onto 5 mg risedronate tablets, each tablet weighing 500 mg and each containing:

Active Ingredients:

| Risedronate Sodium | 5 mg* |
|---|---|
| Chelant: | |
| Sodium Citrate | 250 mg |
| Excipient: | |
| Microcrystalline Cellulose | 109.5 mg |
| Croscarmellose Sodium | 25.0 mg |
| Mannitol | 100 mg |
| Magnesium stearate | 0.5 mg |
| Polyvinylpyrrolidone | 10 mg |
| Purified Water | 100.0 mg |

*This amount is calculated on a risedronate anhydrous monosodium salt basis.

Tablets having the composition set forth above are prepared as follows:

The risedronate sodium, sodium citrate, microcrystalline cellulose, croscarmellose sodium, mannitol and polyvinylpyrrolidone are passed through a mill and added to a blender equipped with an intensifier bar. The mixture is blended for approximately ten minutes with the intensifier bar on and granulated with purified water for 15 minutes. The mixture is dried overnight at 30° C., passed through a mill. The magnesium stearate is screened and added to the blender. The blend is mixed for approximately 3 minutes with the intensifier bar off. The blend is compressed into tablets using a suitable tablet press.

Example VIII

Time Dependent Delivery Tablets Containing Risedronate and EDTA

Time dependent delivery tablets containing risedronate and EDTA are made by preparing a coating composition and compressed tablets containing risedronate and EDTA, and then applying said coating composition to said tablets.

A coating composition is prepared containing the following excipients, per tablet:
A. Coating Suspension
Excipients:

| | |
|---|---|
| Carnauba Wax | 80 mg |
| Beeswax | 35 mg |
| Polyoxyethylene sorbitan monooleate | 11 mg |
| Hydroxypropylmethylcellulose | 24 mg |
| Purified Water | 500 mL |

The coating is prepared using the following method:

The carnauba wax, beeswax, polyoxyethlyene sorbitan monooleate, and hydroxypropylmethylcellulose are added to the purified water at 60° C. and mixed for 3 hours. The resulting coating mixture is screened and mixed throughout the coating process. The core tablets are transferred to the coating pan and preheated with occasional jogging. Tablets are coated, using a typical pan coating process until the required quantity of coating solution (at 60° C.) has been applied. Tablets are then cooled and collected in suitable containers.

A coating weight gain of 30% (total solids) is applied by spraying the above composition onto compressed tablets containing risedronate and EDTA, prepared in Part B below.

B. Compressed Tablets Containing Risedronate and EDTA

The coating suspension prepared in Part A above is sprayed onto 35 mg risedronate tablets, each tablet weighing 500 mg and each containing:
Active Ingredients:

| | |
|---|---|
| Risedronate Sodium | 35 mg* |
| Chelant: | |
| Disodium EDTA | 150 mg |
| Excipients: | |
| Microcrystalline cellulose | 50 mg |
| Spray Dried Lactose | 245 mg |
| Sodium starch glycolate | 15 mg |
| Magnesium stearate | 5 mg |

*This amount is calculated on a risedronate anhydrous monosodium salt basis.

Tablets having the composition set forth above are prepared as follows:

The risedronate sodium, EDTA disodium, microcrystalline cellulose, Spray dried lactose and sodium starch glycolate are passed through a mill and added to a blender equipped with an intensifier bar. The mixture is blended for approximately ten minutes with the intensifier bar on. The magnesium stearate is screened and added to the blender. The blend is mixed for approximately 3 minutes with the intensifier bar off. The blend is compressed into tablets using a suitable tablet press.

Example IX

Bacterial Enzyme Triggered Tablets Containing Alendronate and Tartaric Acid

Bacterial Enzyme Triggered tablets containing alendronate and tartaric acid are made by preparing a tablet blend and compressing into tablets.
A. Compressed Tablets Containing Alendronate and Tartaric Acid The 70 mg alendronate, each tablet weighing 680 mg and each containing:
Active Ingredients:

| | |
|---|---|
| Alendronate Sodium | 70.0 mg* |
| Excipients: | |
| Guar Gum | 300.0 mg |
| Hydroxypropylmethylcellulose | 50.0 mg |
| Tartaric Acid | 250.0 mg |
| Stearic acid | 10 mg |

*This amount is calculated on a alendronic acid anhydrous trihydrate basis.

Tablets having the composition set forth above are prepared as follows:

The alendronate sodium, guar gum, hydroypropylmethylcellulose and tartaric acid are passed through a mill and added to a blender equipped with an intensifier bar. The mixture is blended for approximately ten minutes with the intensifier bar on. The blend is compressed into slugs on a rotary tablet press. The slugs are passed through a mill and collected. The stearic acid is added to the blender and the blend is mixed for approximately 3 minutes. The blend is compressed into tablets using a suitable tablet press.

The compressed tablets are coated with the layers described in Example VI using the same methods for coating.

Example X

Enteric-Coated Tablets Containing Alendronate and EDTA

Enteric-coated tablets containing alendronate and EDTA are made by preparing a coating composition and compressed tablets containing alendronate and EDTA, and then applying said coating composition to said tablets.

An enteric coating composition is prepared in the form of a lacquer containing the following excipients, per tablet:
A. Enteric Coating Suspension
Excipients:

| | |
|---|---|
| Eudragit L 30 D-55 ® (wet basis) (manufactured by Röhm Pharma GmbH and Co. KG, Darmstadt, Germany) | 120 mg |
| Triethylcitrate | 10 mg |
| Talc | 10 mg |

| | |
|---|---|
| Red Iron Oxide | 0.01 mg |
| Simethicone emulsion | 0.8 mg |
| Purified Water | 100 mg |

The enteric coating is prepared using the following method:

The talc and red iron oxide are added to a portion of purified water and mixed until uniform. The triethylcitrate and the simethicone emulsion are added with continuous mixing. The resulting pigment suspension is next passed through a screen or a suitable mill to break up agglomerates. The Eudragit L 30 D-55® is screened and then added to a suitable vessel and diluted with a portion of the purified water. The pigment suspension is then added to the diluted Eudragit suspension and mixed until uniform.

In a suitable coating pan, the compressed tablets (10 kg) containing alendronate and EDTA, described below, are warmed to about 30-35° C. The enteric coating suspension is sprayed onto the tablets at approximately 30 grams per minute. When the spray cycle is completed, the temperature is reduced and the tablets are removed and dried at 30-35° C. for approximately 1 hour.

A coating weight gain of 19% (total solids) is applied by spraying the above composition onto compressed tablets containing alendronate and EDTA, prepared in Part B below.

B. Compressed Tablets Containing Alendronate and EDTA

The enteric coating suspension prepared in Part A above is sprayed onto 70 mg alendronate tablets, each tablet weighing 300 mg and each containing:

Active Ingredients:

| | |
|---|---|
| Alendronate sodium | 70 mg* |
| Chelant: | |
| Disodium EDTA | 100 mg |
| Excipients: | |
| Microcrystalline cellulose | 119.5 mg |
| Crospovidone | 9 mg |
| Magnesium stearate | 1.5 mg |

*This amount is calculated on an alendronic acid basis.

Tablets having the composition set forth above are prepared as follows:

The tablets are prepared by sieving the alendronate active ingredient and the EDTA with ½ of the microcrystalline cellulose into a twin shell blender. The blend is then mixed until uniform. Then, ½ of the magnesium stearate is added and the blend is mixed further. The blend is then is roller compacted and milled. The remaining microcrystalline cellulose and crospovidone are added and mixed until uniform. The remaining magnesium stearate is then added and mixed until adequate lubrication is achieved. Tablets are then compressed on a rotary tablet press.

Example XI

Enteric-Coated Tablets Containing Ibandronate and Citric Acid

Enteric-coated tablets containing ibandronate and citric acid are made by preparing a coating composition and compressed tablets containing ibandronate and citric acid, and then applying said coating composition to said tablets.

An enteric coating composition is prepared in the form of a lacquer containing the following excipients, per tablet:

A. Enteric Coating Suspension

Excipients:

| | |
|---|---|
| Eudragit L 30 D-55 ® (wet basis) (manufactured by Röhm Pharma GmbH and Co. KG, Darmstadt, Germany) | 240 mg |
| Triethylcitrate | 20 mg |
| Talc | 10 mg |
| Titanium dioxide | 1.0 mg |
| Simethicone emulsion | 1.6 mg |
| Purified Water | 250 mg |

The enteric coating is prepared using the following method:

The talc and titanium dioxide are added to a portion of purified water and mixed until uniform. The triethylcitrate and the simethicone emulsion are added with continuous mixing. The resulting pigment suspension is next passed through a screen or a suitable mill to break up agglomerates. The Eudragit L 30 D-55® is screened and then added to a suitable vessel and diluted with a portion of the purified water. The pigment suspension is then added to the diluted Eudragit suspension and mixed until uniform.

In a suitable coating pan, the compressed tablets (10 kg) containing ibandronate and Citric Acid, described below, are warmed to about 30-35° C. The enteric coating suspension is sprayed onto the tablets at approximately 30 grams per minute. When the spray cycle is completed, the temperature is reduced and the tablets are removed and dried at 30-35° C. for approximately 1 hour.

A coating weight gain of 17% (total solids) is applied by spraying the above composition onto compressed tablets containing Ibandronate and citric acid, prepared in Part B below.

B. Compressed Tablets Containing Ibandronate and Citric Acid

The enteric coating suspension prepared in Part A above is sprayed onto 100 mg Ibandronate tablets, each tablet weighing 600 mg and each containing:

Active Ingredients:

| | |
|---|---|
| Ibandronate sodium | 100 mg* |
| Chelant: | |
| Citric acid | 350.0 mg |
| Excipients: | |
| Microcrystalline cellulose | 132.0 mg |
| Crospovidone | 15.0 mg |
| Magnesium stearate | 3.0 mg |

*This amount is calculated on an ibandronic acid basis.

Tablets having the composition set forth above are prepared as follows:

The tablets are prepared by sieving the ibandronate active ingredient and the citric acid with ½ of the microcrystalline cellulose into a twin shell blender. The blend is then mixed until uniform. Then, ½ of the magnesium stearate is added and the blend is mixed further. The blend is then roller compacted and milled. The remaining microcrystalline cellulose and crospovidone are added and mixed until uniform. The remaining magnesium stearate is then added and mixed until adequate lubrication is achieved. Tablets are then compressed on a rotary tablet press.

Example XII

Enteric-Coated Tablets Containing Risedronate and EDTA

Enteric-coated tablets containing risedronate and EDTA are made by preparing a coating composition and compressed tablets containing risedronate and EDTA, and then applying said coating composition to said tablets.

An enteric coating composition is prepared in the form of a lacquer containing the following excipients, per tablet:

A. Enteric Coating Suspension
Excipients:

| | |
|---|---|
| Eudragit S100 ® (dry basis) (manufactured by Röhm Pharma GmbH and Co. KG, Darmstadt, Germany) | 12.9 mg |
| Dibutyl Phthalate | 2.59 |
| Talc | 3.54 mg |
| Red Iron Oxide | 1.37 mg |
| Isopropyl alcohol | 110.7 mg |
| Acetone | 24.74 mg |
| Purified Water | 3.1 mg |

The enteric coating is prepared using the following method:

The purified water, approximately 80% of the isopropyl alcohol, and the Eudragit S100 are combined while mixing to form a solution. After mixing for at least 60 minutes, the acetone, dibutyl phthalate, and remaining isopropyl alcohol are added while mixing. Mixing continues through the remainder of the preparation. Ferric oxide and talc are added to the solution and the resulting suspension is then mixed for at least one hour. The coating solution is mixed for at least one hour before production. The core tablets are transferred to the coating pan and preheated with occasional jogging. Tablets are coated using a typical pan coating process until the required quantity of coating solution has been applied. Tablets are then cooled and collected in suitable containers.

A coating weight gain of 8.5% (total solids) is applied by spraying the above composition onto compressed tablets containing risedronate and EDTA, prepared in Part B below.

B. Compressed Tablets Containing Risedronate and EDTA

The enteric coating suspension prepared in Part A above is sprayed onto 35 mg risedronate tablets, each tablet weighing 240 mg as prepared according to Example IB.

Example XIII

Capsules Containing Enteric-Coated Beads

Capsules containing enteric-coated beads are prepared by preparing enteric-coated beads, and then encapsulating them using a gelatin capsule. The beads consist of inert sugar spheres that are coated with a polymeric film which contains risedronate and EDTA and are prepared using the procedure in Part A below. The beads are next enteric-coated using the procedure described in Part B below.

A. Risedronate- and EDTA-Coated Beads

| Component | mg/capsule |
|---|---|
| Risedronate Sodium | 30* |
| Disodium EDTA | 100 |
| Sugar Spheres, 20-25 mesh | 115.6 |
| Hydroxypropylmethylcellulose | 25 |
| Polyethylene Glycol 3350 | 2.5 |
| Purified Water | 700 |

*This amount is calculated on a risedronate anhydrous monosodium salt basis.

The risedronate- and EDTA-coated beads are prepared as follows:

The purified water is heated and the hydroxypropylmethylcellulose is slowly added. When the hydroxypropylmethylcellulose is dispersed, the polyethylene glycol is added and the solution is allowed to cool to 30° C. or less. The risedronate and EDTA are then passed through a mill, if needed, to break up any agglomerates, and then mixed with the polymer solution until uniform.

In a suitable coating column, the sugar spheres are warmed to approximately 35° C. and then the risedronate and EDTA coating suspension prepared above is sprayed on by applying a coating 136% weight gain to the beads. When the spray cycle is completed, the air is turned off and the beads are cooled to room temperature.

B. Enteric-Coated Beads

| Component | mg/capsule |
|---|---|
| Risedronate Sodium- and EDTA-coated beads (prepared in Part A above) | 273.1 |
| Eudragit L 30 D-55 ® (wet basis) | 106 |
| Talc USP | 16.9 |
| Triethyl Citrate NF | 3.2 |
| Simethicone Emulsion USP | 2.1 |
| Yellow Ferric Oxide NF | 0.04 |
| Purified Water | 225 |

The talc is added and the yellow ferric oxide is added to a portion of the purified water and mixed until uniform. The triethyl citrate and the simethicone emulsion are added with continued mixing. The resulting pigment suspension is then passed through a screen or a suitable mill to break up agglomerates. The Eudragit L 30 D-55® is screened and then added to a suitable vessel and diluted with a portion of the purified water. The pigment suspension is then added to the diluted Eudragit suspension and mixing is continued.

In a suitable coating column the risedronate- and EDTA-coated beads are warmed to the appropriate temperature. The enteric coating suspension having the composition described in part B is sprayed on the beads. When the spray cycle is completed, the air is turned off. The coated beads are stored at 25-30° C. for a minimum of 12 hours before encapsulating. The beads are encapsulated utilizing a hard shell gelatin capsule using an appropriate capsule filler.

Example XIV

Enteric-Coated Tablets Containing Risedronate and EDTA

Enteric-coated tablets containing risedronate and EDTA are made by preparing a coating composition and compressed tablets containing risedronate and EDTA, and then applying said coating composition to said tablets.

An enteric coating composition is prepared in the form of a lacquer containing the following excipients, per tablet:

A. Enteric Coating Suspension
Ingredients:

| | |
|---|---|
| Eudragit L 30 D-55 ® (wet basis) (manufactured by Röhm Pharma GmbH and Co. KG, Darmstadt, Germany) | 47.8 mg |
| Triethylcitrate | 2.15 mg |
| Talc | 7.17 mg |
| Red Iron Oxide | 0.07 mg |
| Simethicone emulsion (30%) | 0.14 mg |
| Polysorbate 80 | 0.14 mg |
| Purified Water | 102.6 mg |

The enteric coating is prepared using the following method:

A pigment suspension is prepared by adding polysorbate 80, ground ferric oxide, and talc to approximately two-thirds of the purified water while mixing. The suspension is mixed for at least two hours. The 30% simethicone emulsion and the remaining water are added to the pigment suspension and mixed for at least 45 minutes. The Eudragit L30 D-55® solution and triethyl citrate are combined and mixed for at least 45 minutes. The pigment suspension is then added to the Eudragit solution and mixed for 30 to 60 minutes. The resulting coating suspension is screened and mixed throughout the coating process. The core tablets are transferred to the coating pan and preheated with occasional jogging. Tablets are coated, using a typical pan coating process until the required quantity of coating solution has been applied. Tablets are then cooled and collected in suitable containers.

A coating weight gain of 10% (total solids) is applied by spraying the above composition onto compressed tablets containing risedronate and EDTA, prepared in Part B below.

The enteric coating suspension prepared in Part A above is sprayed onto 35 mg risedronate tablets, each tablet weighing 240 mg and prepared as in Example IB.

Example XV

Enteric-Coated Soft Gelatin Capsules Containing Risedronate and Disodium EDTA

Enteric-coated capsules containing risedronate and EDTA are made by preparing a coating composition and soft gelatin capsules containing risedronate and EDTA, and then applying said coating composition to said soft gelatin capsules.

An enteric coating composition is prepared in the form of a lacquer containing the following excipients, per tablet:

A. Enteric Coating Suspension
Excipients:

| | |
|---|---|
| Eudragit L 30 D-55 ® (wet basis) (manufactured by Röhm Pharma GmbH and Co. KG, Darmstadt, Germany) | 200.0 mg |
| Dibutyl phthalate | 10.0 mg |
| Talc | 30.0 mg |
| Red Iron Oxide | 0.25 mg |
| Simethicone emulsion (30%) | 0.50 mg |
| Polysorbate 80 | 0.50 mg |
| Purified Water | 350 mg |

The enteric coating is prepared using the following method:

A pigment suspension is prepared by adding polysorbate 80, ground ferric oxide, and talc to approximately two-thirds of the purified water while mixing. The suspension is mixed for at least two hours. The 30% simethicone emulsion and the remaining water are added to the pigment suspension and mixed for at least 45 minutes. The Eudragit L 30 D-55 solution and dibutylphthalate are combined and mixed for at least 45 minutes. The pigment suspension is then added to the Eudragit solution and mixed for 30 to 60 minutes. The resulting coating suspension is screened and mixed throughout the coating process. The soft gelatin capsules are transferred to the coating pan and preheated with occasional jogging. The soft gelatin capsules are coated, using a typical pan coating process until the required quantity of coating solution has been applied. Capsules are then cooled and collected in suitable containers.

A coating weight gain of 13% (total solids) is applied by spraying the above composition onto soft gelatin capsules containing risedronate and EDTA, prepared in Part B below.

B. Soft Gelatin Capsules Containing Risedronate and EDTA

The enteric coating suspension prepared in Part A above is sprayed onto 50 mg risedronate soft gelatin capsules, each weighing 764 mg and each containing:

Fill Composition

| | |
|---|---|
| Risedronate sodium | 50 mg* |
| Oleoyl Macrogol-6 Glycerides | 370 mg |
| Colloidal Silicon Dioxide | 5 mg |
| Disodium EDTA | 125 mg |
| Total | 550 mg |
| Gel Shell Composition | |
| Gelatin | 123.4 mg |
| Glycerin | 44.1 mg |
| Anhydrized Liquid Sorbitol (Sorbitol Special, 76%) | 27.1 mg |
| Purified Water | 17.1 mg |
| Titanium dioxide | 1.0 mg |
| FD&C Red No. 40, E129 | 0.96 mg |
| FD&C Blue No. 1, E133 | 0.30 mg |
| Total | 214 mg |
| Total Capsule weight | 764 mg |

*This amount is calculated on a risedronate anhydrous monosodium salt basis.

Soft gelatin capsules having the composition set forth above are prepared as follows:

The Oleoyl Macrogol-6 Glycerides is added to a suspension tank equipped with an overhead mixer. The risedronate sodium, disodium EDTA, colloidal silicon dioxide are passed through a mill and added to the Oleoyl Macrogol-6 Glycerides with continued mixing. The mixture is blended for approximately 60 minutes. The blend is then deaerated and ready for filling into capsules. With mixing, the glycerin, sorbitol special, and purified water are combined in a heated vacuum vessel. Heat is applied until the temperature reaches at least 80° C., then the gelatin is added and mixed for 75 minutes. The gel mass is examined for complete dissolution of particles. If needed continued heating and mixing is applied until there is no visual evidence of undissolved particles. The gel mass is deaerated, then the titanium dioxide, FD&C Red No. 40 and FD&C Blue No. 1 are added with continued mixing. The gel mass is discharged into heated gel holding tanks for subsequent processing. The fill material is then encapsulated on a soft gelatin capsule filler.

Example XVI

Enteric-Coated Tablet for Releasing Citric Acid in the Jejunum and Risedronate in the Ascending Colon An enteric-coated layered tablet containing risedronate sodium in one layer and citric acid in a separate layer is designed so that the citric acid is released in the jejunum and the risedronate is released in the ascending colon. The tablet is prepared according to the following method:

Active Layer:

| Component | mg/tablet |
| --- | --- |
| Risedronate sodium | 50 mg* |
| Hydroxypropylmethylcellulose | 100 mg |
| Starch 1500 | 90 mg |
| Microcrystalline Cellulose | 50 mg |
| Stearic Acid | 10 mg |
| Purified water | 60 mg |

*This amount is calculated on a risedronate anhydrous monosodium salt basis.

A mixture of risedronate sodium, hydroxypropylmethylcellulose, starch 1500, and microcrystalline cellulose is wet granulated in a high shear mixer with purified water. The granulation is then sieved and dried at 30° C. for 12 hours. Then the stearic acid is added and mixed in a low shear mixer until uniform, and the granulation is discharged into a fiber drum.

Citric Acid Layer:

| Component | mg/tablet |
| --- | --- |
| Citric acid | 150 mg |
| Lactose, Hydrous | 100 mg |
| Polyvinylpyrrolidone | 10 mg |
| Microcrystalline Cellulose | 50 mg |
| Stearic Acid | 10 mg |
| Purified water | 65 mg |

A mixture of citric acid, lactose, polyvinylpyrrolidone and microcrystalline cellulose is wet granulated in a high shear mixer with purified water. The granulation is then sieved and dried at 30° C. for 12 hours. Then the stearic acid is added and mixed in a low shear mixer until uniform then the granulation is discharged into a fiber drum. Tablets are compressed at a weight of 620 mg on a layer tablet press.

The enteric coating has the following composition per tablet:

| Component | mg/tablet |
| --- | --- |
| Eudragit L100 ® | 62 |
| Triethylcitrate | 12.5 |
| Isopropyl alcohol | 600 |
| Purified water | 100 |

The triethyl citrate is added to the purified water and isopropyl alcohol with continued mixing. The Eudragit L 100® is added with continued mixing. In a suitable coating pan, the compressed layered tablets (10 kg) containing risedronate in one layer and citric acid in a separate layer are warmed to about 30-35° C. The enteric coating suspension is sprayed onto the tablets at approximately 50 grams/minute. When the spray cycle is completed, the temperature is reduced and the tablets are removed and dried at 30-35° C. for approximately 1 hour.

Example XVII

A 65 kg woman diagnosed with postmenopausal osteoporosis is prescribed the enteric-coated oral dosage form of Example 1, to be taken once weekly, comprising 35 mg risedronate and 100 mg Disodium EDTA. The patient takes the oral dosage form with breakfast once per week. A biopsy of iliac crest bone is taken at two years and reveals an increase in mean wall thickness of the remodeling units compared to her baseline biopsy.

Example XVIII

A 70 kg man diagnosed with prostate cancer and high bone turnover is prescribed the enteric-coated oral dosage form of Example 1, to be taken once weekly, comprising 35 mg risedronate and 150 mg citric acid. The patient takes the oral dosage form once per week, immediately before going to sleep. The patient does not experience upper GI irritation or discomfort.

Example XIX

A randomized, open-label, single-dose, single-center, 8-treatment, parallel-group study is performed to compare absorption of oral, fasted immediate release risedronate sodium tablets with fed and fasted risedronate sodium plus EDTA delivered to different locations in the lower GI tract. The study consists of one 72-hour period.

The following treatments are administered to treatment groups A-H:

| Treatment Group | Number of Subjects | Dose | Delivery/Status |
| --- | --- | --- | --- |
| A | 10 | 35 mg risedronate sodium tablet | Stomach/fasted |
| B | 10 | 35 mg risedronate sodium + 100 mg disodium EDTA | jejunum/fasted |
| C | 10 | 35 mg risedronate sodium + 100 mg disodium EDTA | jejunum/fed |
| D | 10 | 35 mg risedronate sodium + 100 mg disodium EDTA | terminal ileum/fasted |
| E | 10 | 35 mg risedronate sodium + 100 mg disodium EDTA | terminal ileum/fed |
| F | 10 | 35 mg risedronate sodium + 100 mg disodium EDTA | ascending colon/fasted |
| G | 10 | 35 mg risedronate sodium + 100 mg disodium EDTA | ascending colon/fed |
| H | 10 | 35 mg risedronate sodium + 100 mg disodium EDTA | descending colon/fasted |

For fasted administration, subjects fast overnight and the dose is administered in the morning. Subjects continue to fast until the drug is released at the specified site.

For fed administration (Treatment Groups C, E, and G), subjects are fed a light breakfast and at approximately 3 hours later subjects take the study medication. Immediately following the passing of the study medication from the stomach, these subjects eat a breakfast. Subjects continue to fast until 2 hours after the drug is released at the specified site.

Ratio of Fed to Fasted Urine Recovery for Different Sites of Release

| Location of Release | Urinary Recovery (% of dose) Ratio Fed/Fasted |
|---|---|
| Jejunum | 0.959 |
| Ileum | 1.131 |
| Ascending Colon | 1.560 |

A ratio near 1 indicates that the absorption is the same with or without food.

Example XX

Enteric-Coated Tablets Containing Risedronate and EDTA

Enteric-coated tablets containing risedronate are prepared using a similar method as described in Example I. A coating preparation is prepared as described below.

A. Enteric Coating Suspension
Ingredients:

| Eudragit FS30D (wet basis) | 57.6 mg |
|---|---|
| Eudragit FS30D (dry basis) | 17.3 mg |
| Triethylcitrate | 0.86 mg |
| Talc | 5.18 mg |
| Red iron oxide | 0.07 mg |
| Simethicone emulsion (30%) | 0.21 mg |
| Polysorbate 80 | 0.55 mg |
| Purified water | 160.1 mg |

A pigment suspension is prepared by adding polysorbate 80, ground ferric oxide, and talc to approximately two-thirds of the purified water while mixing. The suspension is mixed for at least two hours. The 30% simethicone emulsion and the remaining water are added to the pigment suspension and mixed for at least 45 minutes. The Eudragit FS30D solution and triethylcitrate are combined and mixed for at least 45 minutes. The pigment suspension is then added to the Eudragit solution and mixed for 30 to 60 minutes. The resulting coating suspension is screened and mixed throughout the coating process.

The compressed risedronate tablets as described in Example I are transferred to the coating pan and preheated with occasional jogging. The compressed tablets are coated with the Enteric-Coating Suspension using a typical pan process until the required coating has been applied.

All documents cited are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral dosage form comprising:
   (a) about 150 mg of a bisphosphonate selected from the group consisting of a risedronate and salts thereof;
   (b) from about 55 mg to about 500 mg of an ethylenediaminetetraacetic acid (EDTA) or a pharmaceutically acceptable salt thereof; and
   (c) a delayed release mechanism to deliver the risedronate and the EDTA in the lower gastrointestinal tract.

2. The oral dosage form of claim 1, wherein the bisphosphonate is risedronate sodium.

3. The oral dosage form of claim 2, wherein the EDTA is disodium EDTA.

4. The oral dosage form of claim 3, wherein the disodium EDTA is from about 75 mg to about 250 mg in the oral dosage form.

5. The oral dosage form of claim 4, wherein the oral dosage form is a tablet.

6. The oral dosage form of claim 5, wherein the delayed release mechanism in an enteric coating.

7. The oral dosage form of claim 6, wherein the enteric coating comprises a methacrylic acid copolymer.

8. The oral dosage form of claim 7, wherein the thickness of the enteric coating is between about 10 microns and about 500 microns.

9. The oral dosage form of claim 8, wherein the methacrylic acid copolymer is poly(methacryclic acid, ethyl acrylate) 1:1.

10. The oral dosage form of claim 7, wherein the weight gain of the enteric coating on the tablet is 5% to 50%.

11. The oral dosage form of claim 10, wherein the methacrylic acid copolymer is poly(methacryclic acid, ethyl acrylate) 1:1.

12. The oral dosage form of claim 7, wherein the enteric coating provides proximal release and delivery in the lower gastrointestinal tract.

* * * * *